US005965619A

United States Patent [19]

Pamukcu et al.

[11] Patent Number: 5,965,619
[45] Date of Patent: Oct. 12, 1999

[54] METHOD FOR TREATING PATIENTS HAVING PRECANCEROUS LESIONS WITH SUBSTITUTED INDENE DERIVATIVES

[75] Inventors: Rifat Pamukcu, Spring House, Pa.; Gary A. Piazza, Highlands Ranch, Colo.; Paul Gross; Gerhard Sperl, both of Stockton, Calif.; Klaus Brendel, Tucson, Ariz.

[73] Assignee: Cell Pathways Inc., Horsham, Pa.

[21] Appl. No.: 08/996,944

[22] Filed: Dec. 23, 1997

Related U.S. Application Data

[63] Continuation of application No. 08/662,458, Jun. 13, 1996, abandoned.

[51] Int. Cl.⁶ .......................... A01N 37/10; A01N 37/34; A01N 43/54
[52] U.S. Cl. .......................... 514/569; 514/256; 514/277; 514/365; 514/381; 514/372; 514/231.2; 514/482; 514/506; 514/520; 514/553
[58] Field of Search ..................... 514/569, 256, 514/277, 365, 381, 372, 231.2, 482, 506, 520, 553

[56] References Cited

U.S. PATENT DOCUMENTS

| | | | |
|---|---|---|---|
| 3,161,654 | 12/1964 | Shen | 548/500 |
| 3,312,730 | 4/1967 | Winter | 560/56 |
| 3,325,358 | 6/1967 | Winter et al. | 514/237.5 |
| 3,532,752 | 10/1970 | Shen | 564/323 |
| 3,609,184 | 9/1971 | Miyai et al. | 562/466 |
| 3,622,623 | 11/1971 | Shen et al. | 562/428 |
| 3,631,167 | 12/1971 | Shen | 548/250 |
| 3,642,785 | 2/1972 | Shen et al. | 548/473 |
| 3,647,858 | 3/1972 | Hinkley et al. | 560/11 |
| 3,654,349 | 4/1972 | Shen et al. | 562/428 |
| 3,692,651 | 9/1972 | Sletzinger | 562/428 |
| 3,692,825 | 9/1972 | Conn | 562/428 |
| 3,700,730 | 10/1972 | Hinkley | 562/428 |
| 3,737,455 | 6/1973 | Shen et al. | 562/428 |
| 3,759,987 | 9/1973 | Conn | 562/428 |
| 3,766,259 | 10/1973 | Sletzinger | 562/428 |
| 3,772,282 | 11/1973 | Ford, Jr. | 549/500 |
| 3,812,109 | 5/1974 | Shen et al. | 536/17.9 |
| 3,812,180 | 5/1974 | Shen et al. | 562/427 |
| 3,822,310 | 7/1974 | Shen et al. | 562/428 |
| 3,851,063 | 11/1974 | Shen et al. | 514/569 |
| 3,860,636 | 1/1975 | Shen et al. | 562/8 |
| 3,868,414 | 2/1975 | Shen et al. | 562/427 |
| 3,868,415 | 2/1975 | Jones | 562/428 |
| 3,869,507 | 3/1975 | Jones | 562/428 |
| 3,870,753 | 3/1975 | Tull et al. | 562/428 |
| 3,888,902 | 6/1975 | Shen et al. | 558/413 |
| 3,897,487 | 7/1975 | Jones | 562/428 |
| 3,932,498 | 1/1976 | Shen et al. | 562/428 |
| 3,944,600 | 3/1976 | Tull et al. | 562/428 |
| 3,954,852 | 5/1976 | Shen | 562/428 |
| 3,956,363 | 5/1976 | Shen et al. | 560/108 |
| 3,970,693 | 7/1976 | Tull et al. | 562/428 |
| 3,998,875 | 12/1976 | Tull et al. | 562/428 |
| 4,207,340 | 6/1980 | Gardocki | 514/569 |
| 4,233,457 | 11/1980 | Czaja et al. | 562/428 |
| 4,307,114 | 12/1981 | Dvornik et al. | 514/569 |
| 4,402,979 | 9/1983 | Shen et al. | 514/569 |
| 4,423,074 | 12/1983 | Dvornik et al. | 514/866 |
| 4,423,075 | 12/1983 | Dvornik et al. | 514/569 |
| 4,656,190 | 4/1987 | Shen et al. | 514/529 |
| 4,748,271 | 5/1988 | Meneghin | 562/428 |
| 4,943,587 | 7/1990 | Cetenko et al. | 514/415 |
| 5,112,868 | 5/1992 | Cetenko et al. | 514/618 |
| 5,229,516 | 7/1993 | Musser et al. | 546/172 |
| 5,401,774 | 3/1995 | Pamukcu | 514/569 |
| 5,420,289 | 5/1995 | Musser | 548/159 |

FOREIGN PATENT DOCUMENTS

| | | |
|---|---|---|
| 61-106521 | 5/1986 | Japan. |
| 1178658 | 1/1970 | United Kingdom. |
| 91/06537 | 5/1991 | WIPO. |
| 96/03120 | 2/1996 | WIPO. |
| 96/03987 | 2/1996 | WIPO. |

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology, vol. 24, pp. 83–87 (1983).
Federation Proceedings (1972) of the Federation of American Societies for Experimental Biology abstract Nos. 2044 and 2045.
Gilman, S.C. et al., Nonsteroidal Anti–inflammatory Drugs in Cancer Therapy, (circa 1985), pp. 157–179.
Brogden, R.N. et al., Drugs, vol. 16, pp. 97–114 (1978).
Hucker, H.B. et al., Drug Metabolism & Disposition, vol. 1, No. 6, pp. 721–736 (1973).
Shen, T.Y. et al., Chemical and Biological Studies on Indomethacin, Sulindac and Their Analogs, pp. 107–178 (circa 1975).
Duggan, D.E. et al., Clin. Pharm. & Therapeutics, vol. 21, No. 3, pp. 326–335 (1976).
Duggan, D.E. et al., J. Pharm. & Exper. Therap., vol. 201, No. 1, pp. 8–13 (1977).
Glavin, G.B. et al., Toxicology and Applied Pharmacology, vol. 83, pp. 386–389 (1986).
Moorghen, M. et al., Journal of Pathology, vol. 156, pp. 341–347 (1988).
Moorghen, M. et al., Acta Histochemica, Suppl.–Band XXIX, S. 195–199 (1990).
Bjarnason et al., Gastroenterology, vol. 94, No. 4, pp. 1070–1074 (1988).

*Primary Examiner*—D. Margaret M. Mach
*Attorney, Agent, or Firm*—Robert W. Stevenson

[57] ABSTRACT

Substituted indene derivatives are useful for treating patients having precancerous lesions and for inhibiting the growth of neoplastic cells.

29 Claims, No Drawings

METHOD FOR TREATING PATIENTS HAVING PRECANCEROUS LESIONS WITH SUBSTITUTED INDENE DERIVATIVES

This application is a continuation of application Ser. No. 08/662,458, filed Jun. 13, 1996, now abandoned.

TECHNICAL FIELD

This invention relates to compounds and methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk. of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from preexisting benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those with high risk genetic factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeuticc drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cyto-toxicity of the drugs, include hair loss, weight loss, vomiting and bone marrow immune suppression. Therefore, there is a need to identify new drug candidates for therapy that do not have such serious side effects in humans.

In the last few years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reported to be converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of treating patients with precancerous lesions by administering a pharmacologically effective amount of those compounds described below to a patient in need of such treatment. Such compositions are effective in eliminating and inhibiting the growth of precancerous lesions and neoplasms, but are not characterized by the severe side reactions of conventional NSAIDs.

DETAILED DESCRIPTION OF THE INVENTION

As discussed above, the present invention includes a method for treating a patient having precancerous lesions with the compounds of formula I below:

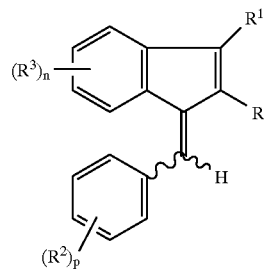

(I)

wherein
  R is H, loweralkyl especially $C_{1-6}$alkyl, for example, niethyl, ethyl, isopropyl, n-propyl, butyl, pentyl or hexyl, trihalcialkyl or cycloalkyl;

$R^1$ is
  (a) —$CHR^4COOR$ wherein $R^4$ is hydrogen, hydroxy, loweralkyl, amino, alkylamino, dialkylamino or benzylamino;
  (b) —$(CH_2)_mR^5$ wherein $R^5$ represents R, OR, SR, S-phenyl (unsubstituted or substituted with one or more of $R^8$, as defined below), SOR, $SO_2R$, CN, —O—COR, —NHCOR, —NRCOOR, —NRCONRR$^4$, —O—CONRR$^4$, —NRR4, halo especially fluoro, or Y, wherein Y is a heterocycle as defined below, e.g., pyrimidinyl, pyridyl, imidazolyl, tetrazolyl, isothiazolyl and morpholinyl; and m is 1 to 4;
  (c) —CH=CHR;
  (d) —$(CH_2)_mCONRR^4$; or
  (e) —CHOH—CHOH—R;
$R^2$ is independently
  (a) —$NHSO_2R^6$ where $R^6$ represents R, —$CF_3$, phenyl unsubstituted or substituted with at least one of $R^8$, for example, phenyl, p-methoxyphenyl, p-chlorophenyl, m-trifluoromethylphenyl or the like;
  (b) hydrogen;
  (c) lower alkyl;
  (d) —$NHCOR^6$
  (e) —$NRR^4$;
  (f) —$OR^7$ wherein $R^7$ is H, R, loweralkenyl especially $C_{1-6}$alkenyl such as —$CH_2$—CH=$CH_2$; lower alkynyl especially $C_{1-6}$alkynyl such as —$CH_2$—C≡CH;
  (g) —O—$(CH_2)_m$—O— when two adjacent $R^2$ are joined together to form a fused ring and where m represents 1, 2 or 3;
  (h) halo especially fluoro, chloro and bromo;
  (i) trihaloalkyl;
  (j) —$SO_2NRR^4$;
  (k) —$SO_2NHY$ wherein Y is a heterocycle as defined below;
  (l) —$SO_2NHX$ wherein X is —$CONH_2$, —$CSNH_2$ or —C(=NH)$NH_2$;
  (m) —$SO_2CF_3$;
  (n) —CN;
  (o) —$SO_2NR^4COR^6$; or
  (p) —$COOR^6$;
$R^3$ is independently
  (a) hydrogen;
  (b) lower alkyl especially $C_{1-6}$alkyl;
  (c) —$OR^7$;
  (d) —O—$(CH_2)_m$—O— when two adjacent $R^3$ are joined together to form a fused ring and wherein m is 1, 2 or 3;
  (e) halo especially F;
  (f) —O—$CH_2$-phenyl or $R^8$-substituted phenyl;
  (g) —$CH_2OR^6$;
  (h) —$SR^6$;
  (i) —S—$CH_2$-phenyl or $R^8$-substituted phenyl;
  (j) —$CH_2$—S—$R^6$;
  (k) —$SOR^6$;
  (l) —$SO_2R^6$;
  (m) —$OCOR^6$;
  (n) —$NRR^4$ or —$NH_2$;
  (o) —$NR^4COOR^6$;
  (p) —$NHCOR^6$; or
  (q) —$OCOOR^6$;
$R^8$ is independently
  (a) hydrogen;
  (b) lower alkyl;
  (c) lower alkoxy;
  (d) amine;

(e) lower alkylamine;
(f) lower di-alkylamine;
(g) halo;
(h) cyano; or
(i) halo substituted lower alkyl;
n is 1, 2 or 3; and p is 1, 2 or 3.

Preferably, the compounds useful in this invention are of the structural Formula (II) below:

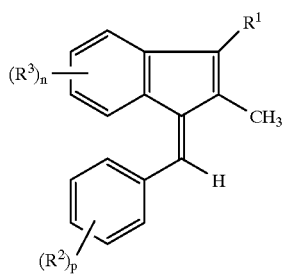

(II)

wherein $R^1$, $R^2$ and $R^3$ are as previously defined.

Even more preferably, the compounds useful in this invention are of the structural Formula (III) below:

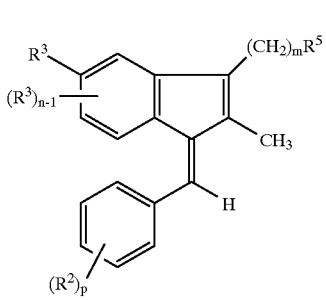

(III)

wherein m, n, p and $R^5$ are as previously defined;

$R^2$ is independently
(a) —$SO_2NRR^4$;
(b) —$SO_2NHX$ wherein X represents —$CONH_2$, —$CSNH_2$, or —$C(=NH)NH_2$;
(c) —$SO_2NHY$ wherein Y represents a heterocycle, e.g.,

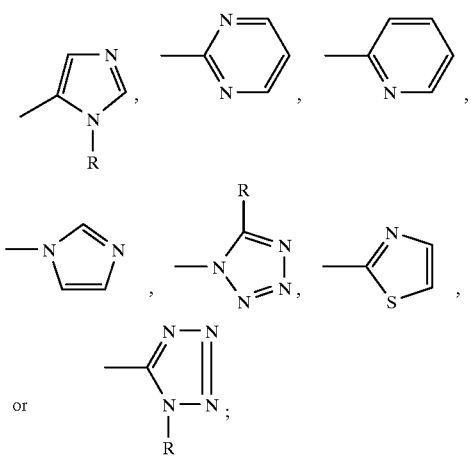

(d) —$SO_2CF_3$;
(e) —$SO_2NHCOR^6$; or
(f) —$OR^7$; and $R^3$ is independently
(a) hydrogen;
(b) loweralkyl;
(c) —$OR^7$;
(d) —$O(CH_2)_m$—O— when two adjacent $R^3$ are joined together to form a fused ring and m is 1, 2 or 3;
(e) —$OCH_2$-phenyl or $R^8$-substituted phenyl;
(f) halo especially —F;
(g) —$SR^6$;
(h) —$OCOR^6$;
(i) —$NHCOR^6$; or
(j) —$OCOOR^6$.

Still more preferably, compounds useful in this invention are of the structural formula (III) above, wherein $R^2$ is independently
(a) —$SO_2NRR^4$; or
(b) —$OR^7$; and p is 3;

$R^3$ is independently
(a) hydrogen;
(b) loweralkyl;
(c) loweralkoxy; or
(d) halo especially —F; and n is 1;

$R^5$ is a heterocycle, especially tetrazolyl.

The present invention also is a method of treating a patient with precancerous lesions by administering a pharmacologically effective amount of a pharmaceutical composition that includes the compounds of formula I, II and III, wherein $R^1$ through $R^8$ are as defined above (preferably without therapeutic amounts of an NSAID), to a patient in need of such treatment.

The present invention is also a method of treating individuals with precancerous lesions by administering a pharmacologically effective amount of an enterically coated pharmaceutical composition that includes compounds of formula I, II and III.

The present invention is also a method of inhibiting the growth of neoplastic cells by exposing these cells to an effective amount of a compound of Formula I, II and III.

In still another aspect, the invention is a method of inducing apoptosis in human cells by exposing those cells to an effective amount of the compound of formula I, II and III above where such cells are sensitive to this compound.

Additionally, in yet another aspect, the invention is a method of treating a patient having a disease which would benefit from regulation of apoptosis by treating the patient with an effective amount of the compound of formula I, II and III above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast and/or skin and related conditions (e.g., actinic keratosis, whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

As used herein, the term "halo" or "halogen" refers to chloro, bromo, fluoro and iodo groups, and the termn "alkyl" refers to straight, branched or cyclic alkyl groups. The term "lower alkyl" refers to $C_1$ to $C_8$ alkyl groups.

Compounds of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of this invention excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

The pharmaceutical compositions of this invention are preferably packaged in a container (e.g. a box or bottle, or both) with suitable printed material (e.g. a package insert) containing indications, directions for use, etc.

The foregoing may be better understood from the following examples, that are presented for purposes of illustration and are not intended to limit the scope of the invention.

Preparation of the Compounds

The compounds of formula I, II and III can be easily prepared from the corresponding indenes and the appropriately substituted benzaldehydes. For example:

SCHEME 1
Illustration for Example 1

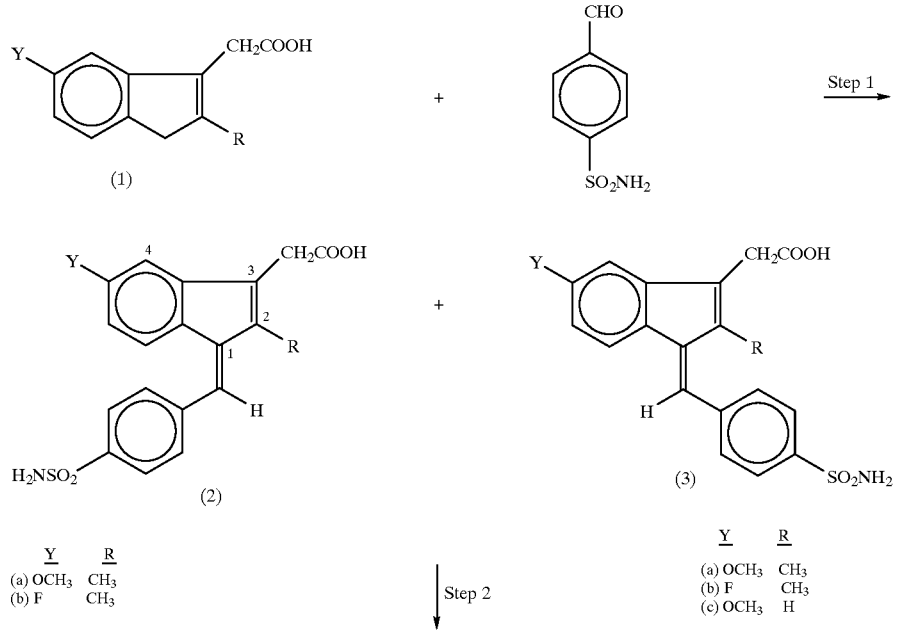

-continued

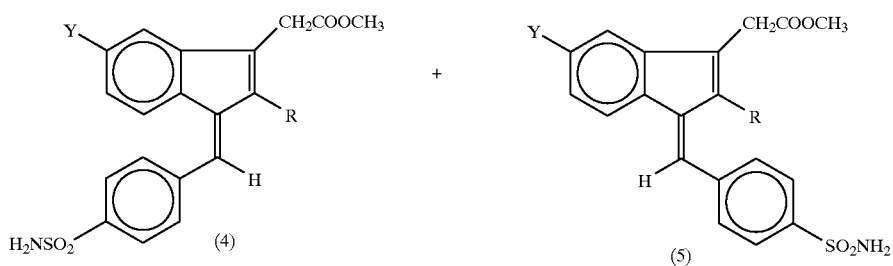

(4)
| Y | R |
|---|---|
| (a) OCH₃ | CH₃ |
| (b) F | CH₃ |

(5)
| Y | R |
|---|---|
| (a) OCH₃ | CH₃ |
| (b) F | CH₃ |
| (c) OCH₃ | H |

Step 3A/3B

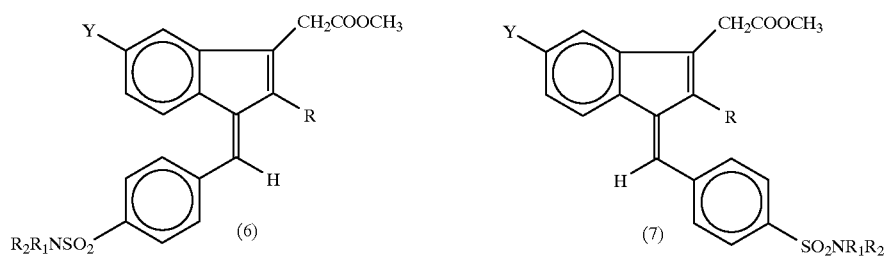

(6)
| Y | R | R₁ | R₂ |
|---|---|---|---|
| (a) OCH₃ | CH₃ | H | CH₃ |
| (b) OCH₃ | CH₃ | CH₃ | CH₃ |
| (c) OCH₃ | CH₃ | H | COCH₃ |

(7)
| Y | R | R₁ | R₂ |
|---|---|---|---|
| (a) OCH₃ | CH₃ | H | CH₃ |
| (b) F | CH₃ | H | CH₃ |
| (c) OCH₃ | H | H | CH₃ |

PART B)

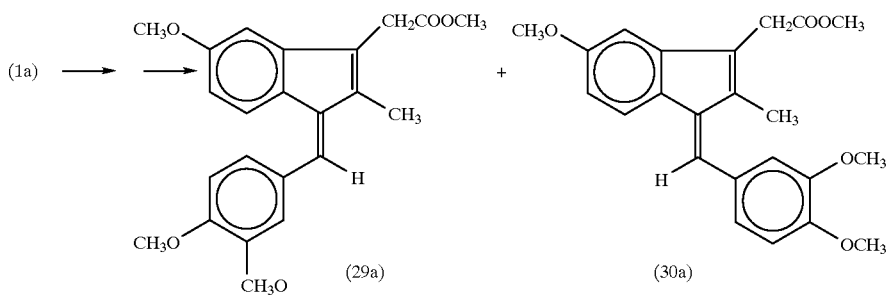

EXAMPLE 1

Z(cis) and E(trans) 1-(4-Aminosulfonylphenyl) methylene-5-substituted-2-methyl-1H-3-indenylacetic acids and analogs

Step 1

Preparation of E and Z 1-(4-aminosulfonylphenyl) methylene-5-methoxy-2-methyl-1H-3-indenylacetic acids (2a and 3a)

To a solution of 5-methoxy-2-methyl-3-indenylacetic acid (1a) (3.95 g) in 90% methanol (24 ml) containing 85% potassium hydroxide (2.7 g) was added a solution of p-aminosulfonylbenzaldehyde (3.70 g) in 90% methanol (24 ml). The resulting mixture was refluxed under nitrogen for 4–6 hours. A solution of 50% aqueous acetic acid (50 ml) was then added to the reaction mixture during 40 minutes at 50°–60° C. The crystals were collected after aging at 15° C. for 1 hour. The crude product was recrystallized five times from acetone-hexane to give pure Z form of 1-(4-aminosulfonylphenyl) methylene-5-methoxy-2-methyl-1H-3-indenylacetic acid (2a) (4.0 g, 57%): m.p. 224°–225° C.

The E acid enriched mother liquor from above (E:Z=1:4, 100 mg) was purified via preparative TLC using 500 μm silica gel plates (3–4 mg per plate) developed 5–6 times with 10% methanol in chloroform to give the E form of 1-(4-amino sulfonylphenyl) methylene-5-methoxy-2-methyl-1H-3-indenyl acetic acid (3a); m.p. 223°–225° C.

Step 2

Preparation of E and Z methyl 1-(4-aminosulfonylphenyl) methylene-5-methoxy-2-methyl-1H-3-indenylacetate (4a and 5a)

A solution of the E acid 3a (950 mg) and toluenesulfonic acid monohydrate (200 mg) in methanol (60 ml) was refluxed for 1–2 hours. The solution was filtered and the filtrate was concentrated to 30 ml. After cooling at 0° to 5° C. for 1 hour, the crystals were collected and dried. The crude ester was recrystallized from acetonitrile to give the pure E methyl 1-(4-aminosulfonylphenyl) methylene-5-methoxy-2-methyl-1H-3-indenylacetate 5a (850 mg, 86%): m.p. 169.5°–171.0° C.

In the same manner, the Z acid 2a was converted to the Z methyl 1-(4-aminosulfonylphenyl) methylene-5-methoxy-2-methyl-1H-3-indenylacetate (4a): m.p. 179.5°–181.0° C.

Following substantially the same procedures as described in Steps 1 and 2, but starting with 5-fluoro-2-methyl-3-indenylacetic acid, the following analogs were prepared:

(1) Z-1-(4-Aminosulfonylphenyl) methylene-5-fluoro-2-methyl-1H-3-indenylacetic acid (2b); m.p. 242.5°–244.0° C.

(2) Z Methyl 1-(4-aminosulfonylphenyl) methylene-5-fluoro-2-methyl-1H-3-indenylacetate (4b); m.p. 183°–184° C.

(3) E-Methyl 1-(4-aminosulfonylphenyl)methylene-5-fluoio-2-methyl-1H-3-indenylacetate (5b); m.p. 206.5°–208.5° C.

Step 3a

N-Methylation of 4a and 5a with diazomethane to form methyl 1-(4-(N-methylaminosulfonyl)phenyl) methylene-5-methoxy-2-methyl-1H-3-indenylacetate and its N,N-dimethyl derivative A solution of 4a (100 mg) in methanol (20 ml) was treated with excess diazomethane ether solution to give two products. They are separated via preparative tlc using 1500 μm silica gel plates developed 3 times with 5% ethyl acetate in chloroform to give Z methyl 1-(4-(N-methylaminosulfonyl) phenyl) methylene-5-methoxy-2-methyl-1H-3-indenylacetate (6a) (30 mg, 29% yield): m.p. 167°–169° C. and Z methyl 1-(4-(N,N-dimethylaminosulfonyl)-phenyl) methylene-5-methoxy-2-methyl-1H-3-indenylacetate (6b) (60 mg, 56% yield): m.p. 163°–164° C.

Following the same procedure as described in Step 3a but starting with 5a or 5b, the following compounds were prepared:

(1) E Methyl 1-(4-(N-methylaminosulfonyl)phenyl) methylene-5-methoxy-2-methyl-1H-3-indenylacetate (7a): m.p. 151.5°–153.5° C.

(2) E Methyl 1-[4-(N-methylaminosulfonyl)phenyl]-methylene-5-fluoro-2-methyl-1H-3-indenylacetate (7b): m.p. 168.5°–170.0° C.

Step 3b

Acetylation of 4a to form Z methyl 1-[4-(N-acetylaminosulfonyl)phenyl]methylene-5-methoxy-2-methyl-1H-3-indenylacetate (6c)

To a solution of 4a (100 mg) in pyridine (5 ml) was added acetic anhydride (2 ml). The mixture was heated at 110° C. for 1 hour and concentrated in vacuo. The crude mixture was purified via preparative TLC using 2000 μm silica gel plates developed with 30% ethyl acetate in chloroform. The isolated product was recrystallized from acetone-hexane to give pure Z methyl 1-[4-(N-acetylaminosulfonyl)phenyl] methylene-5-methoxy-2-methyl-1H-3-indenylacetate (55 mg, 50%): m.p. 172.5°–174.5° C.

Following the same procedure as described in Steps 1–3, but starting with an appropriate substrate, there were prepared the following compounds:

(1) From 5-methoxy-2-methyl-1H-3-indenylacetic acid and 3,4-dimethoxybenzaldehyde to Z methyl 1-(3,4-dimethoxyphenyl)methylene-5-methoxy-2-methyl-1H-3-indenylacetate (29a); m.p. 101°–103° C. and E methyl 1-(3,4-dimethoxyphenyl)methylene-5-methoxy-2-methyl-1H-3-indenylacetate (30a); m.p. 131°–133° C. (Scheme B)

(2) From 5-methoxy-1H-3-indenylacetic acid and 4-aminosulfonylbenzaldehyde to the following compounds:
 (a) E 1-(4-aminosulfonylphenyl)methylene-5-methoxy-1H-3-indenylacetic acid (3c); m.p. 211°–213° C.
 (b) E Methyl 1-(4-aminosulfonylphenyl)methylene-5-methoxy-1H-3-indenylacetate (5c); m.p. 174°–176° C.
 (c) E Methyl 1-[4-(N-methylsulfonylphenyl) methylene-5-methoxy-1H-3-indenylacetate (7c); m.p. 151°–152.5° C.

SCHEME II
Illustration for Example 2

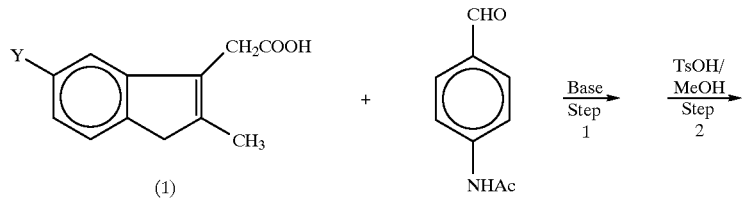

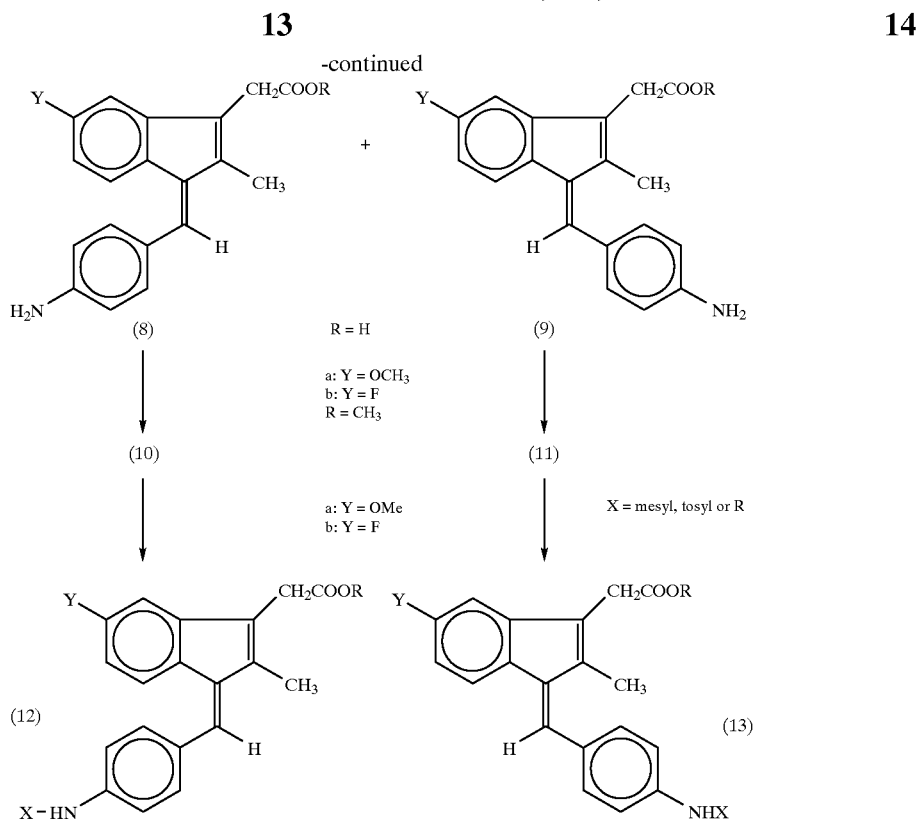

a: Y = OCH₃
b: Y = F
R = CH₃

X = mesyl, tosyl or R a: Y = OMe
b: Y = F

EXAMPLE 2

E and Z 1-(4-Substituted aminophenyl)methylene-5-substituted-2-methyl-1H-3-indenylacetic acids and analogs

Step 1

Preparation of Z 1-(4-aminophenyl)-methylene-5-fluoro-2-methyl-1H-3-indenylacetic acid (8b)

Following the procedure of Example 1, Step 1, but substituting for the compound 1a and p-aminosulfonylbenzaldehyde used therein, an equivalent amount of 5-fluoro-2-methyl-3-indenylacetic acid and p-acetamidobenzaldehyde, there was obtained Z 1-(4-aminophenyl)-methylene-5-fluoro-2-methyl-1H-3-indenylacetic acid (8b); m.p. 214.0°–215.5° C.

Step 2

Preparation of Z methyl 1-(4-aminophenyl)-methylene-5-fluoro-2-methyl-1H-3-indenylacetate (10b)

Following the procedure of Example 1, Step 2, but substituting the compound 3a used therein, an equivalent of 8b, there was obtained Z methyl 1-( 4-aminophenyl) methylene-5-fluoro-2-methyl-1H-3-indenylacetate(10b), m.p. 102.5°–103.5° C.

Step 3

Mesylation of 10b to form Z methyl 1-(4-(N-mesylaminophenyl))methylene-5-fluoro-2-methyl-1H-3-indenylacetate (12b)

To a solution of compound 10b (100 mg) in methylene chloride (20 ml) at 5–10° C. was added dropwise pyridine (55 mg) and then methanesulfonylchloride (80 mg). The mixture was stirred at room temperature for 3½ hours. Purification of the mixture via preparative tlc gave pure Z methyl 1-(4-(N-mesylaminophenyl))methylene-5-fluoro-2-methyl-1H-3-indenylacetate (12b) (110 mg, 88% yield); m.p. 160°–162° C.

Following similar procedures as described in Example 2, Steps 1–3, there was obtained Z methyl 1-(4-(N-mesylaminophenyl))methylene-5-methoxy-2-methyl-1H-3-indenylacetate (12a); m.p. 159°–160° C.

SCHEME III
Illustration for Example 3

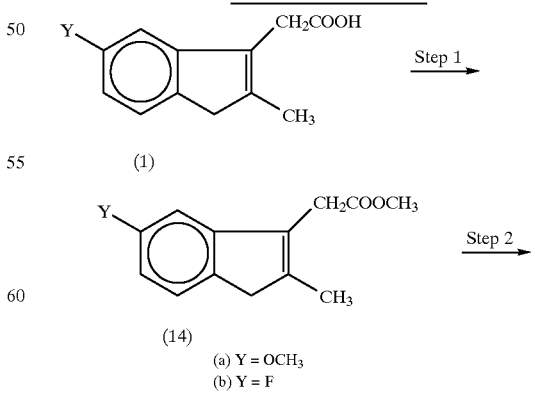

(a) Y = OCH₃
(b) Y = F

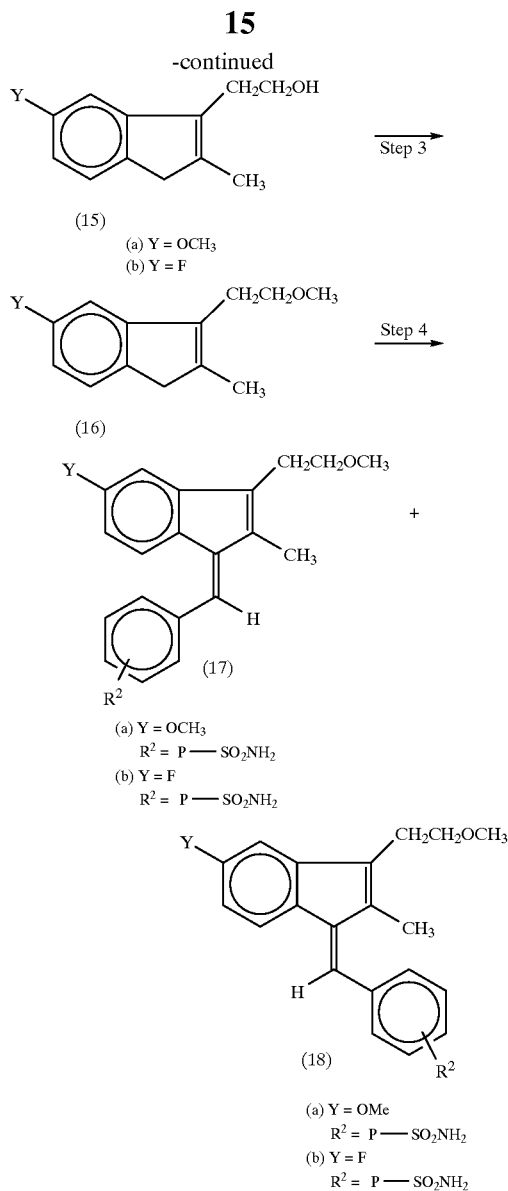

room temperature for 1.5 hours. Excess $LiAlH_4$(LAH) was destroyed with saturated $Na_2SO_4$ solution. The organic phase was concentrated in vacuo, and the crude product was purified via silica gel column chromatography eluting with methylene chloride. The product was recrystallized from hexane to give 5-fluoro-2-methyl-1H-3-indenyl-(2-hydroxy)ethane (15b) (14.9 g, 63% yield): m.p. 65°–66.5° C.

Step 3

Diazomethane methylation of 15b to methyl 5-fluoro-2-methyl-1H-3-indenyl-(2-methoxy)-ethane (16b)

To a solution of compound 15b (1.84 g) in methylene chloride (50 ml) containing 5 drops of $BF_3$-etherate was added a solution of freshly prepared diazomethane ether solution (80 ml, from nitrosomethyl urea). The solution was stirred for ½ hour at room temperature and passed through a short column to remove most of the impurities, and the crude product isolated was used directly in the next step.

Step 4

Preparation of Z and E 1-(4-aminosulfonylphenyl) methylene-5-fluoro-2-methyl-1H-3-indenyl-(2-methoxy)ethane (17b and 18b)

Following the procedure of Example 1, Step 1, but substituting for the compound 1a used therein, an equivalent of 16b, there were produced in 57% yield Z-1-(4-aminosulfonylphenyl)-methylene-5-fluoro-2-methyl-1H-3-indenyl-(2-methoxy)ethane (17b), m.p. 145°–147° C. and E 1-(4-aminosulfonylphenyl)-methylene-5-fluoro-2-methyl-1H-3-indenyl-(2-methoxy)ethane (18b), m.p. 185°–186° C.

Following the same procedures as described in Step 1–4, the following compounds were prepared:

(1) 5-methoxy-2-methyl-1H-3-indenyl-(2-hydroxy)ethane (15a).

(2) Z-1-(4-aminosulfonylphenyl)methylene-5-methoxy-2-methyl-1H-3-indenyl-(2-methoxy)ethane (17a), m.p. 161.5°–162.5° C.

(3) E-1-(4-aminosulfonylphenyl)methylene-5-methoxy-2-methyl-1H-3-indenyl-(2-methoxy)ethane (18a), m.p. 138.5°–140.0° C.

EXAMPLE 3

E and Z 1-(Substituted phenyl)methylene-5-substituted-2-methyl-1H-3-indenyl-(2-methoxy)ethane

Step 1

Preparation of methyl 5-fluoro-2-methyl-1H-3-indenylacelate (14b)

Following the procedure of Example 1, Step 2, but substituting the compound 3a used therein, an equivalent of 1b, there was produced methyl 5-fluoro-2-methyl-3-indenylacetate (14b) as an oil, which was used in the next step without further purification.

Step 2

LAH reduction of 14b to form 5-fluoro-2-methyl-1H-3-indenyl-(2-hydroxy)ethane (15b)

To a solution of 14b (24 g) in dry THF (300 ml), $LiAlH_4$ (6.9 g) was added in portions. The mixture was stirred at

SCHEME IV
Illustration for Example 4

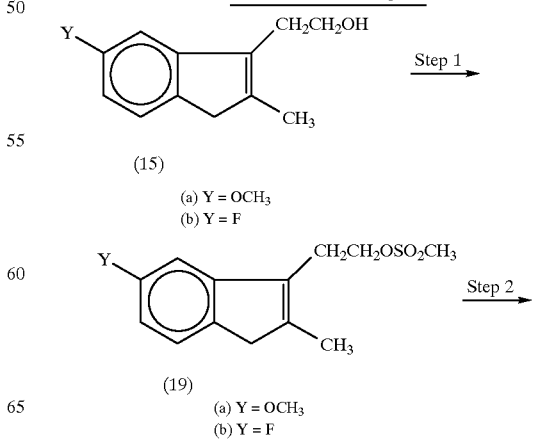

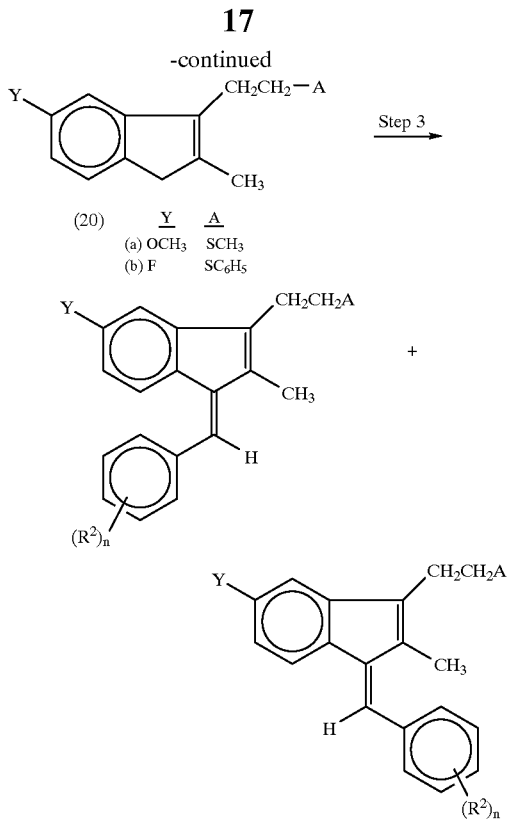

When R=OCH$_3$; R$_n^2$=p-SO$_n$NH$_2$(n=1 or 2)
(21a) A=SCH$_3$
(22a) A=SCH$_3$
(23a) A=SC$_6$H$_5$
(24a) A=SC$_6$H$_5$
(25a)

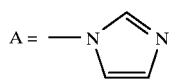

(26a)

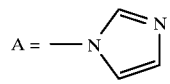

(27a) A=OH
(28a) A=OH

EXAMPLE 4

E and Z 1(4-Aminosulfonyiphenyl)methylene-5-substituted-2-methyl-1H-3-indenyl-(2-methanesulfonyloxy)ethane

Step 1

Preparation of 2-methyl-5-methoxy-1H-3-indenyl-(2-methanesulfonyloxy)ethane (19a)

To a solution of the alcohol 15a (6.0 g) and triethyl amine (6.5 ml) in methylene chloride (60 ml) at room temperature was added a solution of methanesulfonyl chloride (3.0 ml) in methylene chloride (30 ml) dropwise. The mixture was stirred at room temperature for 30 minutes and the precipitates were removed by filtration. The filtrate was evaporated to dryness and the residue was purified via a silica gel column to give 2-methyl-5-methoxy-1H-3-indenyl-(2-methanesulfonyloxy)ethane (19a) (5.7 g, 68% yield): m.p. 84.5°–86.0° C.

Following the same procedure of Step 1 but starting with 15b, there was prepared 5-fluoro-2-methyl-1H-3-indenyl-(2-methanesulfonyloxy)ettiane (19b): m.p. 65.0°–66.5° C.

Step 2

Preparation of 2-methyl-5-methoxy-1H-3-indenyl-(2-methylthio)ethane (20a)

To a saturated solution of methyl mercaptan in absolute ethanol (50 ml) containing potassium tert-butoxide (0.994 g) was added the mesylate 19a (2.5 g). The reaction mixture was refluxed for 30 minutes and evaporated to dryness. The residue was purified via preparative tlc using 1500 μm silica gel plates developed with 20% hexane in methylene chloride to give pure 2-methyl-5-methoxy-1H-3-indenyl-(2-methylthio)ethane (20a) (1.79 g, 86% yield).

Following the same procedure of Step 2, 19b was converted by reaction with phenylmercaptan to 5-fluoro-2-methyl-1H-3-indenyl-(2-phenyithio)ethane (20b).

Step 3

Preparation of Z and E 1-(4-aminosulfonylphenyl) methylene-5-methoxy -2-methyl-1H-3-indenyl-(2-methylthio)ethane (21a and 22a)

Following the procedure of Example 1, Step 1, but substituting the compound 1a used therein an equivalent amount of 20a, there was obtained Z 1-(4-aminosulfonylphenyl)methylene-5-methoxy-2-methyl-1H-3-indenyl-(2-methylthio)ethane (21a): m.p. 178.5°–180.5° C. and E 1-(4-aminosulfonylphenyl)methylene-5-methoxy-2-methyl-1H-3-indenyl-(2-methylthio)ethane (22a): m.p. 172.5°–173.5° C.

Following the same procedures as described in Steps 1–3, there were prepared the following compounds:

(1) Z 1-(4-aminosulfonylphenyl)methylene-5-methoxy-2-methyl-1H-3-indenyl-(2-phenylthio)ethane (23a).

(2) E 1-(4-aminosulfonylphenyl)methylene-5-methoxy-2-methyl-1H-3-indenyl-(2-phenylthio)ethane(24a).

(3) Z 1-(4-aminosulfonylphenyl)methylene-5-methoxy-2-methyl-1H-3-indenyl-[2-(N-imidazolyl)]ethane (25a): m.p. 240.0°–242.0° C.

(4) E 1-(4-aminosulfonylphenyl)methylene-5-methoxy-2-methyl-1H-3-indenyl-[2-(N-imidazolyl]ethane (26a): m.p. 197.0°–199.0° C.

(5) Z 1-(4-aminosulfonyl)methylene-5-methoxy-2-methyl-1H-3-indenyl-(2-hydroxy)ethane (27a): m.p. 170.0°–171.5° C.

(6) E 1-(4-aminosulfonyl)methylene-5-methoxy-2-mnethyl-1H-3-indenyl-(2-hydroxy)ethane (28a): m.p. 185.5°–187.0° C.

SCHEME V
Illustration for Example 5

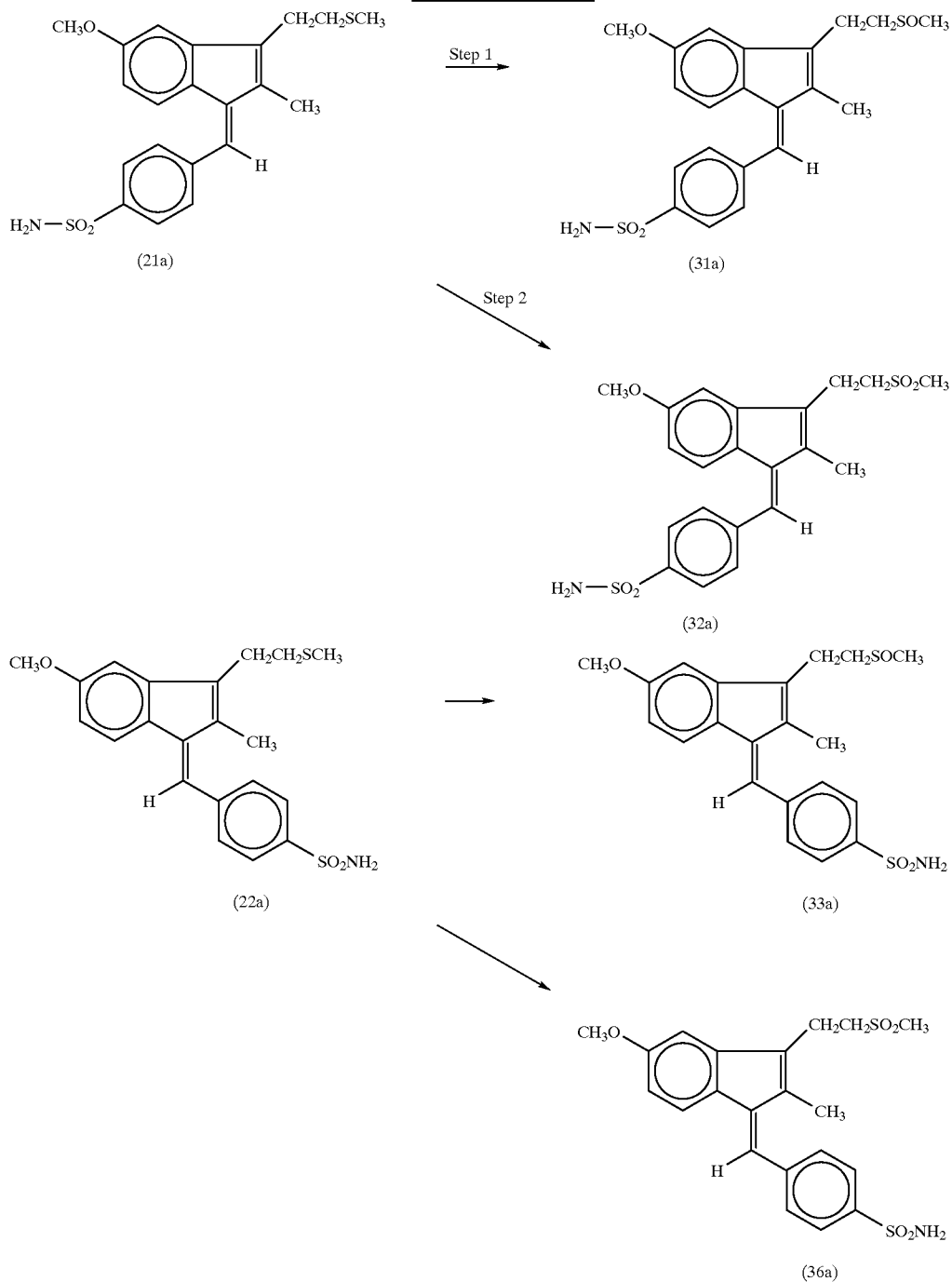

EXAMPLE 5
E and Z 1-(4-Aminosulfonylphenyl)methylene-5-methoxy-2-methyl-1H-3-indenyl-(2-methylsulfinyl) and -(2-methylsulfonyl) ethanes

Step 1
Preparation of Z 1-(4-aminosulfonylphenyl)methylene-5-methoxy-2-methyl-1H-3-indenyl-(2-methylsulfinyl)ethane (31a)

To a solution of 21a (250 mg) in methanol (35 ml) at 0°–5° C. was added a solution of m-chloroperbenzoic acid (90 mg) in methanol (3 ml). The solution was stirred at 5° C. for ½ hour and room temperature for 1 hour. Purification of the crude product via preparative tlc 1000 mm silica gel plates developed three times with 2.5% methanol in methylene chloride gave pure Z 1-(4-aminosulfonylphenyl)methylene-5-methoxy-2-methyl-1H-3-indenyl-(2-methylsulfinyl)ethane (31a) (140 mg, 54% yield): m.p. 205.0°–207.0° C.

Step 2

Preparation of Z 1-(4-aminosulfonylphenyl) methylene-5-methoxy-2-methyl-1H-3-indenyl-(2-methoxysulfonyl)ethane (32a)

Following the procedure of Example 5, Step 1, but substituting one equivalent of MCPBA used therein, by two equivalents of MCPBA there was obtained Z 1-(4-aminosulfonylphenyl)methylene-5-methoxy-2-methyl-1H-3-indenyl-(2-methylsulfonyl)ethane (32a): m.p. 181.0°–182.5° C.

Following the same procedures as described in Example 5, Steps 1–2, but starting with the E form (22a), there were prepared the following compounds:
 (1) E 1-(4-aminosulfonylphenyl)methylene-5-methoxy-2-methyl-1H-3-indenyl-(2-methylsulfinyl)ethane (33a): m.p. 189.0°–190.5° C.
 (2) E 1-(4-aminosulfonylphenyl)methylene-5-methoxy-2-methyl-1H-3-indenyl-(2-methylsulfonyl)ethane (34a): m.p. 190.0°–192.0° C.

SCHEME VI
Photoisomerization illustration for Example 6

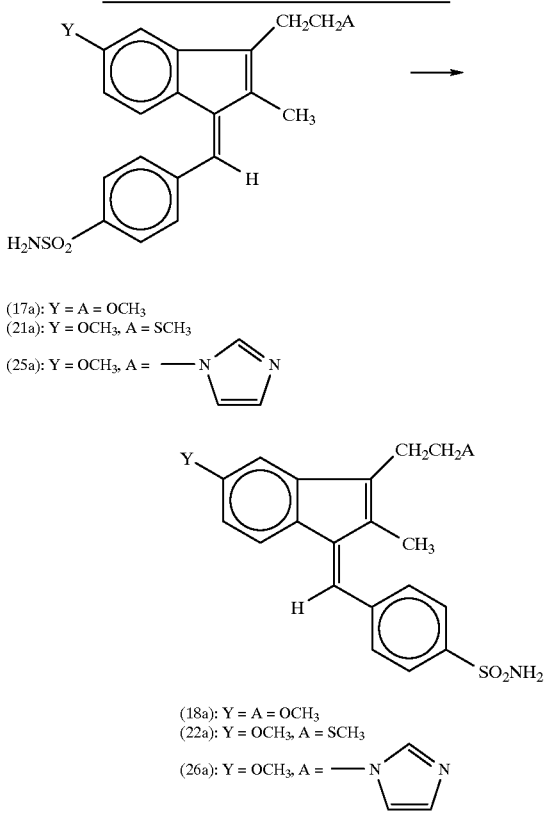

EXAMPLE 6

Photoisomerization of Z form indenes to E form indenes

Method A

A solution of the Z methyl ether, Z 1-(4-aminosulfonylphenyl)-methylene-5-methoxy-2-methyl-1H-3-indenyl-(2-methoxy)ethane (17a) (650 mg) and benzophenone (2.0 g) in acetonitrile was degassed 2–3 times in a pyrex round-bottomed flask and irradiated with a 3000 A lamp under nitrogen for 89 hours. The resulting photolysate was purified via preparative TLC using 1000 $\mu$m silica gel plate (40 mg per plate) developed 3–5 times with 3% acetone in methylene chloride to give E 1-(4-aminosulfonylphenyl)methylene-5-methoxy-2-methyl-1H-3-indenyl-(2-methoxy)ethane (18a): (66 mg, 10% yield): m.p. 138.5°–140.0° C.

Method B

A solution of the Z methyl ether, E 1-(4-aminosulfonylphenyl)-methylene-5-methoxy-2-methyl-1H-3-indenyl-(2-methoxy)ethane (17a) (700 mg) and benzophenone (3.5 g) was irradiated with a medium pressure Hanovia lamp (450 watt) through a quartz well for 75 minutes under nitrogen. Following the work up procedure of Method A, there was obtained E 1-(4-aminosulfonylphenyl)methylene-5-methoxy-2-methyl-1H-3-indenyl-(2-methoxy)ethane (18a) (90 mg, 13% yield): m.p. 139.5°–140.0° C.

Similarly, the Z imidazol derivative, 1-(4-aminosulfonylphenyl)methylene-5-methoxy-2-methyl-1H-3-indenyl-[2-(N-imidazolyl)]ethane (25a) was converted to E 1-(4-aminosulfonylphenyl)methylene-5-methoxy-2-methyl-1H-3-indenyl-[2-(N-imidazolyl)]ethane (26a); m.p. 216.0°–217.0° C.

Additional compounds of formula I can be prepared as follows:

EXAMPLE 7

α-(2-Methyl-5-methoxy-3-indenyl) acetonitrile

The following materials are added together in a reaction vessel: 2-methyl-6-methoxyindanone (8.84 g, 0.05 mol), cyano acetic acid (4.7 g, 0.055 mol), glacial acetic acid (3.0 g, 0.05 mol), ammonium acetate (0.77 g, 0.01 mol), and benzene (7 ml). The mixture is then heated and stirred at an internal temperature of 100–110° C. for 23 hours. The majority of the benzene and water which is formed is removed. The reaction is then continued for 3 hours at 130–135° C. The mixture is then cooled to room temperature and diluted with 50 ml of methylene chloride. This methylene chloride solution is then washed with two 50 ml portions of water and then dried over sodium sulfate and evaporated in vacuo. Methyl alcohol is then added to the residue and stirred and the product filtered (M.P. 108–109° C.).

When α-cyanopropionic acid is used in place of cyano acetic acid in the above example, then the product is α-(2-methyl-5-methoxy-3-indenyl)-propionitrile.

EXAMPLE 8

α-(1-p-chlorobenzylidenyl-2-methyl-5-methoxy-3-indenyl)-acetonitrile

To a solution of 25 ml of 90% methanol containing 2.24 g (0.04 mol) of potassium hydroxide is added 4 g (0.02 mol) of a α-(2-methyl-5-methoxy-3-indenyl)-acetonitrile followed by 4.26 g (0.03 mol) of p-chlorobenzaldehyde. The mixture is stirred and refluxed under a nitrogen atmosphere for 5 hours. The solution is then cooled to 60° C. and 25 ml of 50% acetic acid added. This solution is then cooled to 10° C. for 1 hour and the crude product filtered, washed three times with 15 ml portions of 50% acetic acid and then with water. The product is then dried in vacuo.

EXAMPLE 9

5-(1-p-chlorobenzylidenyl-2-methyl-5-methoxy-3-indenyl-methyl)-tetrazole

A mixture of 6.42 g (0.02 mol) of 1-p-chloro-benzylidene-5-methoxy-2-methyl-3-indenyl-acetonitrile, 1.7 g (0.026 mol) of sodium azide and 1.4 g (0.25 mol) of ammonium chloride in 55 ml of dry dimethylformamide is heated for 16 hours at 120° C. under nitrogen. The reactive mixture is then concentrated in vacuo and the residue dissolved in 75 ml of 2.5 N sodium hydroxide and diluted with 150 ml of water. The aqueous solution is then washed with ether, acidified and extracted with methylene chloride. The methylene chloride extracts are dried over sodium sulfate and concentrated in vacuo to give the desired product.

EXAMPLE 10

α-(1-p-chlorobenzylidenyl-2-methyl-5-dimethylamino-3-indenyl)-propionitrile

To a cooled suspension of α-(1-p-chlorobenzylidenyl-2-methyl-5-dimethylamino-3-indenyl)-propioamide 8.8 g (0.024 mol) in 50 ml of phosphorus oxychloride is added 4.8 g (0.048 mol) of triethylamine. This reaction mixture is then refluxed for one hour and then the excess phosphorus oxychloride is evaporated off under reduced pressure. This is then dissolved in chloroform and washed with an aqueous potassium carbonate solution and then with water. The chloroform solution is then dried over sodium sulfate and concentrated in vacuo to give the desired nitrile.

EXAMPLE 11

When the procedure of Example 7 is followed but substituting for 2-methyl-6-methoxyindanone an equimolar amount of the substituted indanones of Table I below, there is obtained each of the corresponding acetonitriles and propionitriles of Table II below:

TABLE I

| | |
|---|---|
| 6-methoxyindanone | 6-dimethylaminoindanone |
| 6-allyloxyindanone | 2-methyl-6-nitroindanone |
| 6-chloroindanone | 2,6-dimethylindanone |
| 6-hydroxyindanone | 2-methylindanone |
| 6-nitroindanone | 2-ethylindanone |
| 6-aminoindanone | 2-ethyl-6-methoxyindanone |
| 6-methylindanone | |

TABLE II

| | |
|---|---|
| α-(5-methoxy-3-indenyl)-acetonitrile | α-(5-methoxy-3-indenyl)-propionitrile, |
| α-(5-allyloxy-3-indenyl)-acetonitrile | α-(5-allyloxy-3-indenyl)-propionitrile, |
| α-(5-chloro-3-indenyl)-acetonitrile | α-(5-chloro-3-indenyl)-propionitrile, |
| α-(5-hydroxy-3-indenyl)-acetonitrile | α-(5-hydroxy-3-indenyl)-propionitrile, |
| α-(5-nitro-3-indenyl)-acetonitrile | α-(5-nitro-3-indenyl)-propionitrile, |
| α-(5-methyl-3-indenyl)-acetonitrile | α-(5-methyl-3-indenyl)-propionitrile, |
| α-(2-methyl-5-nitro-3-indenyl)-acetonitrile | α-(2-methyl-5-nitro-3-indenyl)-propionitrile, |
| α-(2,5-dimethyl-3-indenyl)-acetonitrile | α-(2,5-dimethyl-3-indenyl)-propionitrile, |
| α-(2-methyl-3-indenyl)-acetonitrile | α-(2-methyl-3-indenyl)-propionitrile, |
| α-(2-ethyl-3-indenyl)-acetonitrile | α-(2-ethyl-3-indenyl)-propionitrile, |
| α-(2-ethyl-5-methyl-3-indenyl)-acetonitrile | α-(2-ethyl-5-methyl-3-indenyl)-propionitrile. |

EXAMPLE 12

When the procedure of Example 8 is followed but substituting an equimolar amount of each of the nitriles of Table II, Example 11, for α-(2-methyl-5-methoxy-3-indenyl)-acetonitrile, then the corresponding 1-p-chloro-benzylidenyl compound is synthesized and found in Table III below:

TABLE III

| | |
|---|---|
| α-(1-p-chlorobenzylidenyl-5-methoxy-3-indenyl)acetonitrile | α-(1-chlorobenzylidenyl-5-methoxy-3-indenyl)propionitrile, |
| α-(1-p-chlorobenzylidenyl-5-allyloxy-3-indenyl)acetonitrile | α-(1-p-chlorobenzylidenyl-5-allyloxy-3-indenyl)propionitrile, |
| α-(1-p-chlorobenzylidenyl-5-chloro-3-indenyl)acetonitrile | α-(1-p-chlorobenzylidenyl-5-chloro-3-indenyl)propionitrile, |
| α-(1-p-chlorobenzylidenyl-5-hydroxy-3-indenyl)acetonitrile | α-(1-p-chlorobenzylidenyl-5-hydroxy-3-indenyl)propionitrile, |
| α-(1-p-chlorobenzylidenyl-5-nitro-3-indenyl)acetonitrile | α-(1-p-chlorobenzylidenyl-5-nitro-3-indenyl)propionitrile, |
| α-(1-p-chlorobenzylidenyl-5-methyl-3-indenyl)acetonitrile | α-(1-p-chlorobenzylidenyl-5-methyl-3-indenyl)propionitrile, |
| α-(1-p-chlorobenzylidenyl-2-methyl-5-nitro-3-indenyl)-acetonitrile | α-(1-p-chlorobenzylidenyl-2-methyl-5-nitro-3-indenyl)-propionitrile, |
| α-(1-p-chlorobenzylidenyl-2,5-dimethyl-3-indenyl)-acetonitrile | α-(1-p-chlorobenzylidenyl-2,5-dimethyl-3-indenyl)-propionitrile, |
| α-(1-p-chlorobenzylidenyl-2-ethyl-3-indenyl)-acetonitrile | α-(1-p-chlorobenzylidenyl-2-ethyl-3-indenyl)-propionitrile, |
| α-(1-p-chlorobenzylidenyl-2-ethyl-5-methoxy-3-indenyl)-acetonitrile | α-(1-p-chlorobenzylidenyl-2-ethyl-5-methoxy-3-indenyl)-propionitrile. |

EXAMPLE 13

When the procedure of Example 8 is followed but substituting an equimolar amount of each of the substituted benzaldehydes of Table IV below for p-chlorobenzaldehyde, there is obtained the corresponding 1-substituted benzylidenyl compound:

TABLE IV

| | |
|---|---|
| o-chlorobenzaldehyde | m-trifluoromethylbenzaldehyde |
| m-chlorobenzaldehyde | p-trifluoromethylbenzaldehyde |
| p-chlorobenzaldehyde | p-trifluoromethylthiobenzaldehyde |
| o-fluorobenzaldehyde | m-nitrobenzaldehyde |
| m-fluorobenzaldehyde | p-nitrobenzaldehyde |
| p-fluorobenzaldehyde | p-trifluoromethoxybenzaldehyde |
| p-bromobenzaldehyde | p-dimethylaminobenzaldehyde |
| p-methylthiobenzaldehyde | m-diethylaminobenzaldehyde |
| p-ethylthiobenzaldehyde | p-diethylaminobenzaldehyde |
| p-methylsulfenylbenzaldehyde | |
| p-methylsulfonylbenzaldehyde | |
| p-ethylsulfonylbenzaldehyde | |

EXAMPLE 14

When each of the known corresponding α-indenylamides are substituted for α-(1-p-chlorobenzylidenyl-2-methyl-5-dimethylamino-3-indenyl)-propionamide following the procedure of Example 10, then the corresponding α-indenylnitriles of Table V below are prepared:

TABLE V

α-(1-p-chloromethylbenzylidenyl-5-methoxy-3-indenyl)-propionitrile

α-(1-p-chlorobenzylidenyl-2-methyl-5-dimethylamino-3-indenyl)-acetonitrile

α-(1-p-chlorobenzylidenyl-2-methyl-5-dimethylamino-3-indenyl)-proplonitrile

α-(1-p-chlorobenzylidenyl-2-methyl-5-methoxy-3-indenyl)-acetonitrile

α-(1-p-chlorobenzylidenyl-2-methyl-5-methoxy-3-indenyl)-propionitrile

α-(1-p-chlorobenzylidenyl-2-methyl-5-nitro-3-indenyl)-acetonitrile

α-(1-p-chlorobenzylidenyl-2-methyl-5-nitro-3-indenyl)-propionitrile

α-(1-m-trifluoromethylbenzylidenyl-2 methyl-5-methoxy-3-indenyl)-acetonitrile

α-(1-p-trifluoromethylbenzylidenyl-2-methyl-5-methoxy-3-indenyl)-propionitrile

α-(1-m-chlorobenzylidenyl-2-methyl-5-methoxy-3-indenyl)-acetonitrile

α-(1-o-chlorobenzylidenyl-2-methyl-5-methoxy-3-indenyl)-acetonitrile

α-(1-p-trifluoromethylbenzylidenyl-2-methyl-5-dimethylamino-3-indenyl)-acetonitrile α-(1-p-trifluoromethylthiobenzylidenyl-2-methyl-5-methoxy-3-indenyl)-acetonitrile α-(1-p-trifluoromethoxybenzylidenyl-2-methyl-5-methoxy-3-indenyl)-acetonitrile α-(1-p-dimethylaminobenzylidenyl-2-methyl-5-methoxy-3-indenyl)-acetonitrile α-(1-p-chlorobenzylidenyl-2-methyl-5-amino-3-indenyl)-acetonitrile α-(1-p-chlorobenzylidenyl-2-methyl-5-methylamino-3-indenyl)-acetonitrile α-(1-p-chlorobenzylidenyl-2,5-dimethyl-3-indenyl)-acetonitrile

EXAMPLE 15

When Example 9 is followed but substituting for 1-p-chlorobenzylidenyl-2-methyl-5-methoxy-3-indenylmethylnitrile each of the compounds listed in Table V of Example 14 and Table III of Example 12, there are obtained the, corresponding tetrazoles listed in Table VI below:

TABLE VI 5-(1-p-chloromethylbenzylidenyl-5-methoxy-3-indenylmethyl-α-methyl)-tetrazole 5-(1-p-chlorobenzylidenyl-2-methyl-5-dimethylamino-3-indenylmethyl)--tetrazole 5-(1-p-chlorobenzylidenyl-2-methyl-5-dimethylamino-3-indenylmethyl-α-methyl)-tetrazole 5-(1-p-chlorobenzylidenyl-2-methyl-5-methoxy-3-indenylmethyl)-tetrazole 5-(1-p-chlorobenzylidenyl-2-methyl-5-methoxy-3-indenylmethyl-α-methyl)-tetrazole 5-(1-p-chlorobenzylidenyl-2-methyl-5-nitro-3-indenylmethyl)-tetrazole 5-(1-p-chlorobenzylidenyl-2-methyl-5-nitro-3-indenylmethyl-α-methyl)-tetrazole 5-(1-m-trifluoromethylbenzylidenyl-2-methyl-5-methoxy-3-indenylmethyl)-tetrazole 5-(1-p-trifluoromethylbenzylidenyl-2-methyl-5-methoxy-3-indenylmethyl)-tetrazole 5-(1-m-chlorobenzylidenyl-2-methyl-5-methoxy-3-indenylmethyl)-tetrazole 5-(1-o-chlorobenzylidenyl-2-methyl-5-methoxy-3-indenylmethyl)-tetrazole 5-(1-p-trifluoromethylbenzylidenyl-2-methyl-5-dimethylamiino-3-indenylmethyl)-tetrazole 5-(1-p-trifluoromethylbenzylidenyl-2-methyl-5-methoxy-3-indenylmethyl)-tetrazole 5-(1-p-trifluoromethoxybenzylidenyl-2-methyl-5-methoxy-3-indenylmethyl)-tetrazole 5-(1-p-dimethylaminobenzylidenyl-2-methyl-5-methoxy-3-indenylmethyl)-tetrazole 5-(1-p-chlorobenzylidenyl-2-methyl-5-amino-3-indenylmethyl)-tetrazole 5-(1-p-chlorobenzylidenyl-2-methyl-5-methylamino-3-indenylmethyl)-tetrazole 5-(1-p-chlorobenzylidenyl-2,5-dimethyl-3-indenylmethyl)-tetrazole 5-(1-p-chlorobenzylidenyl-5-methoxy-3-indenylmethyl)-tetrazole 5-(1-p-chlorobenzylidenyl-5-nitro-3-indenylmethyl)-tetrazole 5-(1-p-chlorobenzylidenyl-5-nitro-3-indenylmethyl-α-methyl)-tetrazole 5-(1-p-chlorobenzylidenyl-5-altyloxy-3-indenylmethyl)-tetazole 5-(1-p-chlorobenzylidenyl-5-allyloxy-3-indenylmethyl-α-methyl)-tetrazole 5-(1-p-chlorobenzylidenyl-5-chloro-3-indenylmethyl)-tetrazole 5-(1-p-chlorobenzylidenyl-5-chloro-3-indenylmethyl-α-methyl)-tetrazole 5-(1-p-chlorobenzylidenyl-5-hydroxy-3-indenylmethyl)-tetrazole 5-(1-p-chlorobenzylidenyl-5-hydroxy-3-indenylmethyl-α-methyl)-tetrazole 5-(1-p-chlorobenzylidenyl-5-methyl-3-indenylmethyl)-tetrazole 5-(1-p-chlorobenzylidenyl-5-methyl-3-indenylmethyl-α-methyl)-tetrazole 5-(1-p-chlorobenzylidenyl-2,5-dimethyl-3-indenylmethyl)-tetrazole 5-(1-p-chlorobenzylidenyl-2,5-dimethyl-3-indenylmethyl-α-methyl)-tetrazole 5-(1-p-chlorobenzylidenyl-2-ethyl-3-indenylmethyl)-tetrazole 5-(1-p-chlorobenzylidenyl-2-ethyl-3-indenylmethyl-α-methyl)-tetrazole 5-(1-p-chlorobenzylidenyl-2-ethyl-5-methoxy-3-indenylmethyl)-tetrazole 5-(1-p-chlorobenzylidenyl-2-ethyl-5-methoxy-3-indenylmethyl-α-methyl)-tetrazole

EXAMPLE 16

(Z)-5-fluoro-2-methyl-1-(p-methoxybenzylidene)-3-indenylacetic acid (A) p-Fluoro-α-methylcinnamic acid.

p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140°. After 20 hours, the flask is cooled to 100° C. and poured into 8 l. of water. The precipitate is dissolved by adding potassium hydroxide (302 g) in 2 l. of water. The aqueous solution is extracted with ether, and the ether extracts washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid.

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the filtrate is concentrated in vacuo to give the product, p-fluoro-α-methylhydrocinnamic acid, which was used without weighing in the next step.

(C) 6-Fluoro-2-methylindanone

To 932 g polyphosphoric acid at 70° C. (on the steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and added to 2 l. of water. The aqueous layer is extracted with ether, the ether solution is washed twice with saturated sodium chloride solution, 5% $Na_2CO_3$ solution, water, and is then dried. The ether filtrate is concentrated with 200 g silica-gel, and is added to a five pound silica-gel column packed with 5% ether-petroleum ether. The column is eluted with 5–10% ether-petroleum ether, to give 6-fluoro-2-methylindanone. Elution is followed by TLC.

(D) 5-fluoro-2-methylindanone-3-acetic acid

A mixture of 6-fluoro-2-methylindanone (18.4 g, 0.112 g mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is concentrated, and the residue dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, 500 ml water added, the aqueous solution is washed well with ether and then boiled with charcoal. The aqueous filtrate is acidified to pH 2 with 50% cold hydrochloric acid. The precipitate and dried 5-fluoro-2-methylindenyl-3-acetic acid (m.p. 164–166° C.) is obtained.

(E) (Z)-5-fluoro-2-methyl-1-(p-methoxy-benzylidene)-3-indenylacetic acid 5-fluoro-2-methyl-3-indenylacetic acid (15 g, 0.072 mol), p-methoxybenzaldehyde (12.39 g, 0.091 mol) and sodium methoxide (13.0 g, 0.24 mol) are heated in methanol (200 ml) at 60° C. under nitrogen with stirring for 6 hours. After cooling, the reaction mixture is poured into 750 ml of ice-water, and is acidified with 2.5 N hydrochloric acid. The collected solid is triturated with a little ether to produce (Z)-5-fluoro-2-methyl-1-(-methoxybenzylidene)-3-indenylacetic acid (m.p. 184–186° C.).

EXAMPLE 17

According to the procedure in Example 16, substituted benzaldehydes may be used in place of p-methoxybenzaldehyde in step (E) at the same reaction conditions to obtain corresponding 1-substituted indenyl compounds. Such mono-substituted benzaldehydes are listed in Table IV of Example 13. However, di- and tri-substituted benzaldehydes, such as 3,5-dimethoxybenzaldehyde, 3-chloro-4-methylbenzaldehyde or vanillin, or others as may be commonly available, may also be used. The following Table VII lists some compounds that are obtained by this procedure.

TABLE VII (a) (Z)-5-fluoro-2-methyl-1-benzylidene-3-indenylacetic acid (m.p. 183–185° C.)

(b) (Z)-5-fluoro-2-methyl-1-(4-chlorobenzylidene)-3-indenylacetic acid (m.p. 188–190° C.)

(c) (Z)-5-fluoro-2-methyl-1-(2-methoxybenzylidene)-3-indenylacetic acid (d) (Z)-5-fluoro-2-methyl-1-(3,4,5-trimethoxybenzylidene)-3-indenylacetic acid (m.p. 166–169° C.).

(e) (Z)-5-fluoro-2-methyl-1-(2,4,6-trimethoxybenzylidene)-3-indenylacetic acid (m.p. 206–209° C.)

(f) (Z)-5-fluoro-2-methyl-1-(2,3,4-trimethoxybenzylidene)-3-indenylacetic acid (m.p. 159–162° C.)

(g) (Z)-5-fluoro-2-methyl-1-(2,4,5-trimethoxybenzylidene)-3-indenylacetic acid (m.p. 185–188° C.)

(h) (Z)-5-fluoro-2-methyl-1-(2,6-dichlorobenzylidene)-3-indenylacetic acid (m.p. 208–209° C.)

(i) (Z)-5-fluoro-2-methyl-1-(2,4-dimethoxybenzylidene)-3-indenylacetic acid (j) (Z)-5-fluoro-2-methyl-1-(3,5-dimethoxybenzylidene)-3-indenylacetic acid (k) (Z)-5-fluoro-2-methyl-1-(4-chloro-3,5-dimethoxybenzylidene)-3-indenylacetic acid (l) (Z)-5-fluoro-2-methyl-1-(4-methyl-2,3-dimethoxybenzylidene)-3-indenylacetic acid

EXAMPLE 18

5-Methoxy-2-Methyl-1-(3,4,5-Trimethoxybenzylidene)-3-Indenyl Acetic Acid (A) α-Methyl-β-(p-methylthiophenyl) propionic acid To a solution of 2.3 g (0.1 mol) of sodium in 100 ml of absolute alcohol is added 17.4 g (0.1 mol) of diethyl methylmalonate and 17.3 g (0.1 mol) of p-methylthiobenzylchloride. The mixture is heated under a reflux in a water bath for three hours. The reaction mixture is poured into water, and the aqueous solution is extracted six times with ether and dried. It is then evaporated to yield diethyl methyl-p-methylthiobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for one hour, cooled and then extracted with ether. Evaporation of the ether solution gives α-methyl-β-(p-methylthiophenyl) propionic acid.

In a similar manner, with other substituted malonic esters in place of diethyl methylmalonate and other substituted benzyl halides in place of p-methylthiobenzoyl chloride, the corresponding substituted propionic acids are obtained, for example:

α-methyl-β-(p-methoxyphenyl)propionic acid,

α-allyl-β-(p-nitrophenyl)propionic acid.

(B) 6-methoxy-2-methylindanone

α-Methyl-β-(p-methoxyphenyl)propionic acid (15 g) is added to polyphosphoric acid (170 g) at 50° C. and the mixture is heated at 83–90° C. for two hours. The syrup is poured into iced water, stirred for one-half hour, and then extracted with ether three times. The ether solution is washed with water twice, and with 5% $NaHCO_3$ five times until all the acidic material has been removed. The remaining neutral solution is washed with water and dried over sodium sulfate. Evaporation of the solution gives the indanone as a pale yellow oil.

In a similar manner, other β-aryl propionic acid compounds are converted to the corresponding indanone by the procedure of this example.

(C) Methyl 5-methoxy-2-methyl-3-indenylacetate.

A solution of 13.4 g of 6-methoxy-2-methylindanone and 19.3 g of methyl bromoacetate in 45 ml benzene is added over a period of 5 minutes to 21 g of zinc amalgam (prepared according to Org. Syn. Coll., vol. 3) in 110 ml benzene and 40 ml dry ether. A few crystals of iodine are added to start the reaction, and the reaction mixture is maintained at reflux temperature (ca. 65° C.) with external heating. At 3 hour intervals, two batches of 10 g zinc amalgam and 10 g bromoester are added, and the mixture is then refluxed for 8 hours. After addition of 30 ml ethanol and 150 ml of acetic acid, the mixture is poured into 700 ml of 1:1 aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° C. (bath temp.) (1–2 mm) gives crude methyl(1-hydroxy-2-methyl-methoxy-indenyl)acetate.

A mixture of the above crude hydroxyester, 20 g of p-toluenesulfonic acid monohydrate and 20 g of anhydrous calcium chloride in 250 ml toluene is refluxed overnight. The solution is filtered, and the solid residue is washed with benzene. The combined benzene solution is washed with water, sodium bicarbonate, water and then dried over sodium sulfate. After evaporation, the crude methyl 5-methoxy-2-methyl-3-indenylacetate is chromatographed on acid-washed alumina, and the product is eluted with petroleum ether-ether (v./v. 50–100%).

METHYL 2,6-DIMETHYL-3-INDENYLACETATE

The above reactions of Example 18(C) are repeated except that the starting materials are 2,5-dimethylindanone and methylbromoacetate. Using the same reaction conditions and techniques there is obtained methyl 2,6-dimethyl-3-indenylacetate.

The above reactions of Example 18(C) are repeated except that the starting materials are 6-methylthioindanone and methylbromoacetate. Using the same reaction conditions and techniques, there is obtained methyl 5-methyl-thio-2-methyl-3-indenylacetate.

When any of the other indanones described in the other examples of the specification are used in the above procedure in place of 6-methoxy-2-methylindanone the corresponding methyl ester is obtained.

(D) 5-methoxy-2-methyl-1-(2,3,4-trimethoxybenzylidene)-3-indenyl acetic acid.

To a solution of methyl 5-methoxy-2-methyl-3-indenylacetate 8.7 g (0.037 mol) and 2,3,4-trimethoxybenzaldehyde, 7.99 g (1.1 equivalent) is added 16+ml (2.0+equivalents) of 25% methanolic sodium methoxide. The mixture is stirred at reflux under nitrogen for 2 hours. An equal volume of water is added dropwise and refluxing continues for 30 min. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is crystallized to give 5-methoxy-2-methyl-1-(2,3,4-trimethoxybenzylidene)-3-indenyl acetic acid.

EXAMPLE 19

1-(3,4,5-Trimethoxybenzylidene-2-Methyl-5-Methoxy-3-Indenyl)-Propionic Acid (A) Methyl-α (5-methoxy-2-methyl-3-indenyl) propionate.

The procedure of Example 18C is followed using methyl α-bromopropionate in equivalent quantities in place of methyl bromoacetate used therein. There is obtained methyl α-(1-hydroxy-6-methoxy-2-methyl-1-indenyl)propionate, and it is then dehydrated to methyl α-(5-methoxy-2-methyl-3-indenyl)propionate in the same manner.

(B) α-[1-(3,4,5-trimethoxybenzylidene)-2-methyl-5-methoxy-3-indenyl] propionic acid To a solution of 0.5 g (1.92 mmol) of methyl α-(5-methoxy-2-methyl-3-indenyl) propionate and 0.77 g (3.9 mmol) of 3,4,5-trimethoxybenzaldehyde in 3 ml of anhydrous pyridine is added 1.63 g of a 40% solution of benzyltrimethylammonium hydroxide (Triton-B) in methanol. The resulting red-purple solution is stirred at room temperature overnight.

The reaction mixture is poured into a mixture of ice and water, acidified with 2.5 N HCl, and extracted with ether. The ether solution i:s then washed with 2.5 N HCl until the washing acidifies (once), then with water until neutral. The ether layer is then extracted with 5% $Na_2CO_3$ solution. The $Na_2CO_3$ solution is washed with ether, acidified and extracted with ether. The ether solution is washed with water, dried over $Na_2SO_4$ and concentrated in vacuo to obtain α-[1-(3,4,5-trimethoxybenzylidene)-2-methyl-5-methoxy-3-indenyl] propionic acid.

EXAMPLE 20

1-(2,4,6-Trimethoxybenzylidene)-5-Dimethylamino-2-Methyl-3-Indenyl Acetic Acid (A) Methyl-3-hydroxy-2-methyl-5-nitro-3-indenylacetate The procedure of Example 18C is followed using 2-methyl-6-nitro indanone in equivalent quantities in place of 6-methyoxy-2-methyl-indanone used therein. After the mixture is condensed, 30 ml of ethanol and 50 ml of acetic acid are added. The mixture is then poured into 700 ml of water. Extraction with ether gives methyl 3-hydroxy-2-methyl-5-nitro-3-indenylacetate.

(B) Methyl 5-dimethylamino-2-methyl-3-indenylacetate.

A solution of 0.05 mol of methyl 3-hydroxy-2-methyl-5-nitro-3-indenylacetate, 0.2 mol of 38% aqueous formaldehyde and 2 ml of acetic acid in 100 ml ethanol is reduced catalytically in the presence of a 10% Pd/C catalyst under 40 lb p.s.i. hydrogen pressure at room temperature. The solution is filtered, evaporated and chromatographed on 300 g of silica gel to give methyl 5-dimethylamino-3-hydroxy-2-methyl-3-indenylacetate. The hydroxy ester is then dehydrated to methyl 5-dimethylamino-2-methyl-3-indenylacetate.

(C) 1-(2,4,6-trimethoxybenzylidene)-5-dimethylaminc-2-methyl-3-indenyl acetic acid.

To a solution of 2.5 g of the ester from Part B of this example in 15 ml of 1,2-dimethoxyethane at 0° C. is added 1.95 g of 2,4,6-trimethoxybenzaldehyde followed by 1.1 g of potassium t-butoxide. The reaction mixture is kept in the ice-bath for 4 hours, and then allowed to stand at room temperature for 18 hours. The mixture is diluted with 15 ml of ether and the potassium salt is filtered. The salt is dissolved in 30 ml of water and neutralized with dilute hydrochloric acid to pH 6–6.5. The crude acid precipitated is collected by filtration and re-crystallized to give 1-(2,4,6-trimethoxy-benzylidene)-5-dimethylamino-2-methyl-3-indenyl acetic acid.

EXAMPLE 21

α-(1-(2,4,6-Trimethoxybenzylidene-2-Methyl-5-Fluoro-3-Indenyl)-Propionic Acid

α-[1-(2,4,6-trimethoxybenzylidene)-2-methyl-5-fluoro-3-indenyl]-propionic acid is prepared by the procedures of Examples 19 A and B.

EXAMPLE 22

N-[5-fluoro-2-methyl-1-(3,4,5-trimethoxy-benzylidene)-3-indenylacetyl]glycine (A) Benzyl-N-[5-fluoro-2-methyl-1-(3,4,5-trimethoxybenzylidene)-3-indenylacetyl]-glycinate. The procedure of Example 21 is followed using benzylamine acetate in place of the morpholine to produce the abovie-named compound.

(B) N-[5-fluoro-2-methyl-1-(3,4,5-trimethoxybenzyliden()-3-indenylacetyl]-glycine. Benzyl-N-[5-fluoro-2-methyl-1-(3,4,5-trimethoxybenzylidene)-3-indenylacetyl]-glycinate (0.03 mol) in a mixture of 25 ml of anhydrous ethanol and 2.5 ml of 1 N sodium hydroxide is allowed to stand at room temperature for 18 hours. The solution is diluted with water and extracted with ether. The aqueous layer is acidified with dilute hydrochloric acid and the organic product is extracted with ethyl acetate, washed with water and dried over sodium sulfate. Evaporation of the solution gives N-[5-fluoro-2-methyl-1-(3,4,5-trimethoxybenzylidene)-3-indenylacetic acid, the corresponding indenyl acyl glycine is obtained.

EXAMPLE 23

(A) Sodium 5-fluoro-2-methyl-1-(3,4,5-trimethoxybenzylidene)-3-indenylacetate 5-fluoro-2-methyl-1-(3,4,5-trimethoxybenzylidene)-3-indenylacetic acid (1.79 g, 4.65 mmol) in methanol (10 ml) is added to a solution of sodium methoxide (0.25 g, 4.65 mmol) in methanol (5 ml). The reaction mixture is stirred for 20 minutes and evaporated to dryness to yield sodium 5-fluoro-2-methyl-1-(3,4,5-trimethoxybenzylidene)-3-indenylacetate.

(1) Calcium 5-fluoro-2-methyl-1-(3,4,5-trimethoxybenzylidene)-3-indenylacetate

The above reaction is repeated using 2 moles of acid per mole of calcium methoxide. Using the same reaction conditions and techniques there is obtained calcium 5-fluoro-2-methyl-1-(3,4,5-trimethoxybenzylidene)-3-indenylacetate.

EXAMPLE 24

Methyl (Z)-5-Fluoro-2-Methyl-1-(3,4,5-Trimethoxybeiizylidene-3-Indenyl Acetic Acid (Z)-5-fluoro-2-methyl-1-(3,4,5-trimethoxybenzylidene)-3-indenylacetic acid is prepared by the procedure of Example 17, and converted to the methyl ester derivative by the following procedure. (Z)-5-fluoro-2-methyl-1-(3,4,5-trimethoxybenzylidene)-3-indenylacetic acid (1.00 g, 2.60 mmol) in dichloromethane (50 ml) is allowed to react with excess diazomethane until TLC shows complete reaction. The organic layer is extracted with saturated sodium bicarbonate (3×25 ml), dried with sodium sulfate, and concentrated in vacuo. The resulting oil is crystallized to yield the desired compound. Other methyl esters of compounds of this invention can be prepared in a similar fashion.

EXAMPLE 25

The following tablet composition is illustrative of the compositions of this invention.

Five thousand tablets for oral use, each containing 10 mg of 5-(1-p-chlorobenzylidenyl-2-methyl-5-methoxy-3-indenylmethyl)-tetrazole are prepared from the following types and amounts of materials:

5-(1-p-chlorobenzylidenyl-2-methyl-5-methoxy-3-indenylmethyl)-tetrazole . . . 50 g Lactose, U.S.P. . . . 600 g Sucrose, powdered, U.S.P. . . . 600 g Cornstarch, U.S.P. . . . 150 g The finely powdered materials are mixed well and the mixture is granulated with 10% starch paste. The wet mass is forced through an 8-mesh screen, dried at 45° C. in a forced-air oven and then put through a 12-mesh screen. As lubricant, 15 grams of magnesium stearate is added before compressing into tablets.

The compounds of this invention can be formulated with pharmaceutically acceptable carriers into unit dosage forms in a conventional manner so that the patient in need of therapy for precancerous lesions can periodically (e.g. once or more per day) take a compound according to the method of this invention.

BIOLOGICAL EFFECTS

A) HT-29

These compounds were assayed for their effect on the human colon carcinoma cell line, HT-29 obtained from ATCC, (Rockville, Md.) to ascertain the degree of growth inhibition. Growth inhibition of this cell line is indicative of a benefit on precancerous lesions and neoplasms. The cell line and growth assay employed for these experiments is well characterized, and is used by the United States National Cancer Institute in its screening program for new anti-cancer drugs.

Drug stock solutions were made in 100% DMSO then diluted with RPMI media for cell culture testing. All drug solutions were prepared fresh on the day of testing. The cultured cells were obtained at passage #118 and grown in RPMI media supplemented with 5% fetal calf serum, and 2 mM glutamine, 100 U/ml penicillin, 100 U/ml streptomycin, and 0.25 $\mu$g/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. All experiments involved HT-29 cells between passages 120 and 140. Cells were plated at the following densities to obtain cultures used for the experiments: 500 cells/well for 96 well flat-bottom microtiter plates, 1×10$^6$ cells per 25 cm$^2$ flask.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with six wells per drug concentration. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug.

For each experiment, an $IC_{50}$ value was determined and used for comparative purposes. This value is equivalent to the concentration of drug needed to inhibit tumor cell growth by 50%. $IC_{50}$ values were obtained graphically by connecting the mean values for each drug concentration tested. Each experiment included at least six wells per drug concentration. Concentration was plotted on a log scale on the X-axis. IC$_{50}$ values obtained for the compounds of different Examples are provided in Table 1 below for the HT-29 cell line.

TABLE 1

| EXAMPLE | IC$_{50}$($\mu$M) | CELL LINE |
|---------|-------------------|-----------|
| 16(e)   | 29                | HT-29     |
| 17(a)   | 40                | HT-29     |
| 17(b)   | 58                | HT-29     |
| 17(d)   | 39                | HT-29     |
| 17(e)   | 61                | HT-29     |
| 17(f)   | 40                | HT-29     |
| 17(g)   | 40                | HT-29     |
| 17(h)   | 31                | HT-29     |

(B) Cyclooxygenase (COX) Inhibition

Compounds of this invention, as well as several others (see Table 2 below), were evaluated to determine whether they inhibited the production of prostaglandin according to the procedure below.

COX is involved in the formation of prostaglandins and thromboxane by the oxidative metabolism of arachidonic acid. The compound of Example 1 was evaluated for inhibitory effects on purified COX. The COX was purified from ram seminal vesicles, as described by Boopathy, R. and Balasubramanian, J., 239:371–377, 1988. COX activity was assayed as described by Evans, A. T., et al., "Actions of cannabis constituents on enzymes of arachidonate metabolism anti-inflammatory potential," Biochem. Pharmacol., 36:2035–2037, 1987. Briefly, purified COX was incubated with arachidonic acid (100 uM) for 2.0 min at 37° C. in the presence or absence of test compounds. The assay was terminated by the addition of TCA, and COX activity was determined by absorbance at 530 nm.

TABLE 2

| | Results | |
|---|---|---|
| Compound | Dose | % Inhibition |
| Sulindac Sulfide | (100 $\mu$M dose) | 86 percent inhibition |
| Example 17(d) | (100 $\mu$M dose) | No inhibition |

(C) Apoptosis/Necrosis

Apoptosis and necrosis were measured using an assay that allowed for the simultaneous measurement of both types of cell death based on morphological characteristics of apoptotic cells (i.e., condensed chromatin) and membrane permeability. Drug preparation and cell culture conditions were the same as for the SRB assay described above. Confluent cultures were established in 25 cm$^2$ flasks. The cultures were assayed for apoptosis and necrosis by fluorescent microscopy following labeling with acridine orange and ethidium bromide. Floating and attached cells were collected by trypsinization and washed three times in PBS. One ml aliquots of 1×10$^6$ cells were centrifuged (300 g). The pellet was resuspended in 25 $\mu$l media and 1 $\mu$l of a dye mixture containing 100 $\mu$g/ml acridine orange and 100 $\mu$g/ml ethidium bromide prepared in PBS and mixed gently. Ten $\mu$l of mixture was placed on a microscope slide and covered with a 22 mm$^2$ coverslip and examined under 40× dry objectives using epillumination and filter combination.

An observer blinded to the identity of the treatments scored at least 100 cells per sample. Apoptotic cells were identified by nuclear condensation of chromatin stained by the acridine orange or ethidium bromide, respectively. Necrotic cells were identified by uniform labelling of the cell with ethidium bromide. These results are provided in Table 3 below.

TABLE 3

| Apoptosis and Necrosis Effects for Compounds | | |
|---|---|---|
| Treatment | % Apoptotic Cells | % Necrotic Cells |
| None | 7 | 2 |
| Vehicle (DMSO) | 9 | 3 |
| No. 16(e) (200 $\mu$M) | >90 | — |
| No. 17(a) (300 $\mu$M) | 90 | — |
| No. 17(d) (200 $\mu$M) | >90 | — |
| No. 17(e) (200 $\mu$M) | >90 | — |
| No. 17(f) (200 $\mu$M) | >90 | — |
| No. 17(g) (200 $\mu$M) | >90 | — |
| No. 17(h) (200 $\mu$M) | 60 | 40 |

(D) Organ Culture

The compound of Example No. 17(d) was also tested for its ability to inhibit the incidence of mammary lesions in an organ culture system. This mouse mammary gland organ culture technique has been successfully used by other investigators to study the effects of known cancer-chemopreventative agents such as retinoids and selenium.

Female BALB/c mice, 28 days old, were treated for nine days with a combination of 1 $\mu$g of estradiol and 1 mg of progesterone daily, in order to prime the glands to be responsive to hormones in vitro. The animals were sacrificed and thoracic mammary glands were excised aseptically and incubated for ten days in growth media supplemented with growth-promoting hormones: insulin, prolactin, and hydrocortisone, at 5 $\mu$g/ml each and aldosterone at 1 $\mu$g/ml. A twenty-four hour treatment of 7,12-dimethylbenz(a) anthracene (DMBA, 2 $\mu$g/ml) was carried out between days three and four to induce the formation of mammary lesions. Fully developed glands were deprived of prolactin, hydrocortisone, and aldosterone for 14 days, resulting in the regression of the glands but not the mammary lesions.

In order to evaluate the effects of Compound No. 17(d), it was dissolved in DMSO and added to the culture media supplemented for the duration of the culture period. At the end of the culture period, the glands were fixed in 10% formalin, stained with alum carmine, and mounted on glass slides. The incidence of forming mammary lesions is the ratio of the glands with mammary lesions and glands without lesions. The incidence of mammary lesions in compound 17(d) treated glands was compared with that of the untreated glands. The results obtained are shown in Table 4 below.

The extent of the area occupied by the mammary lesions was quantitated by projecting an image of the gland onto a digitation pad. The area covered by the gland was traced on the pad and considered as 100% of the area, The space covered by each of the unregressed structures was also outlined on the digitization pad and quantitated by the computer.

TABLE 4

| Effect of Compound No. 1 on DMBA-Induced Mammary Lesions in Organ Culture | | | | |
|---|---|---|---|---|
| Drug Concentration ($\mu$M) | No. Glands Per Group | Glands with Lesions | Percent Incidence | Percent Inhibition |
| Vehicle (DMSO) | 15 | 10 | 66.67 | 0 |
| No. 17(d) (10 $\mu$m) | 15 | 5 | 33.33 | 50 |
| No. 17(d) (100 $\mu$m) | 15 | 0 | 0.00 | 100 |

The compounds of this invention can be formulated with pharmaceutically acceptable carriers into unit dosage forms in a conventional manner so that the patient in need of therapy for precancerous lesions can periodically (e.g. once or more per day) take a compound according to the method of this invention. The exact initial dose of the compounds of this invention can be determined with reasonable experimentation.

It will be understood that various changes and modifications can be made in the details of procedure, formulation and use without departing from the spirit of the invention, especially as defined in the following claims.

What is claimed is:

1. A method for treating a patient having precancerous lesions comprising administering a pharmacologically effective amount of a compound of formula I below:

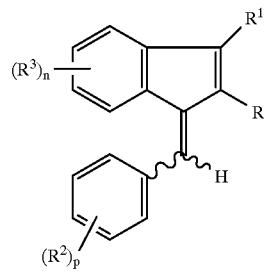

(I)

wherein

R is H, loweralkyl, trihaloalkyl or cycloalkyl;

$R^1$ is —CHR$^4$COOR wherein $R^4$ is hydrogen, hydroxy, loweralkyl, amino, alkylamino or benzylamino; —CH═CHR; —(CH$_2$)$_m$CONRR$^4$; —CHOH—CHOH—R; —(CH$_2$)$_m$R$^5$ wherein R$^5$ represents R, OR, SR, S-phenyl, S-phenyl-(R$^8$)m, SOR, SO$_2$R, CN, —O—COR, —NHCOR, —NRCOOR, —NRCONRR$^4$, —O—CONRR$^4$, —NRR$^4$, halo, or Y, wherein Y is a heterocycle selected from the group consisting of pyrimidinyl, pyridyl, imidazolyl, tetrazolyl, isothiazolyl and morpholinyl, and m is 1 to 4;

$R_2$ is independently —NHSO$_2$R$^6$; hydrogen; lower alkyl; —NHCOR$^6$; —NRR$^4$; —OR$^7$ wherein R$^7$ is H, R, lower alkenyl, lower alkynyl; —O—(CH$_2$)$_m$—O— when two adjacent R$^2$ are joined together to form a fused ring, and where m represents 1, 2 or 3; halo; trihaloalkyl; —SO$_2$NRR$^4$; —SO$_2$NHY wherein Y is a heterocycle as defined; —SO$_2$NHX wherein X is CONH$_2$, —CSNH$_2$ or —C(═NH)NH$_2$; —SO$_2$CF$_3$; —CN; —SO$_2$NR$^4$COR$^6$; or —COOR$^6$;

$R^3$ is independently hydrogen; hydroxy; lower alkyl; lower alkoxy; —OR$^7$; —O—(CH$_2$)$_m$—O— when two adjacent R$^3$ are joined together to form a fused ring and wherein m is 1, 2 or 3; halo; —O—CH$_2$-phenyl or phenyl substituted with R$^8$; —CH$_2$OR$^6$; —SR$^6$; —S—CH$_2$-phenyl or phenyl substituted with R$^8$; —CH$_2$—S—R$^6$; —SOR$^6$; —SO$_2$R$^6$; —OCOR$^6$; —NRR$^4$; —NH$_2$; —NR$^4$COOR$^6$; —NHCOR$^6$; or —OCOOR$^6$;

$R^6$ is selected from the group consisting of R, —CF$_3$, unsubstituted phenyl or phenyl substituted with R$^8$;

$R^8$ is independently hydrogen, lower alkyl, lower alkoxy, amino, lower alkylamino, lower di-alkyl amino, halo, cyano or halo substituted lower alkyl; and n is 1, 2 or 3; p is 1, 2 or 3.

2. The method of claim 1 wherein $R^1$ is —(CH$_2$)$_m$R$^5$.

3. The method of claim 2 wherein $R^5$ is Y.

4. The method of claim 3 wherein $R^5$ is a tetrazolyl substituted with R$^8$.

5. The method of claim 2 wherein $R^2$ is independently lower alkoxy, —SO$_2$NRR$^4$; —SO$_2$NHX wherein X represents —CONH$_2$, —CSNH$_2$, or —C(═NH)NH$_2$; —SO$_2$NHY; —SO$_2$CF$_3$; —SO$_2$NHCOR$^6$; or —OR$^7$.

6. The method of claim 5 wherein $R^2$ is —SO$_2$NRR$^4$.

7. The method of claim 5 wherein $R^2$ is lower alkoxy.

8. The method of claim 2 wherein $R^3$ is independently hydrogen; lower alkyl; —OR$^7$; —O(CH$_2$)$_m$—O— when two adjacent $R^3$ are joined together to form a fused ring and m is 1, 2 or 3; —OCH$_2$-phenyl or R$^8$-substituted phenyl; —F; —SR$^6$; —OCOR$^6$; —NHCOR$^6$; or —OCOOR$^6$.

9. The method of claim 8 wherein $R^3$ is independently hydrogen; hydroxy; lower alkyl; lower alkoxy or —F.

10. The method of claim 9 wherein $R^3$ is independently hydrogen or —F.

11. A method for inhibiting the growth of neoplastic cells comprising exposing the cells to an effective amount of a compound of formula I below:

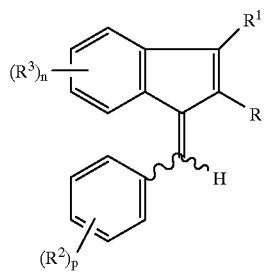

(I)

wherein

R is H, loweralkyl, trihaloalkyl or cycloalkyl;

$R^1$ is —CHR$^4$COOR wherein R$^4$ is hydrogen, hydroxy, loweralkyl, amino, alkylamino or benzylamino; —CH═CHR; —(CH$_2$)$_m$CONRR$^4$; —CHOH—CHOH—R; —(CH$_2$)$_m$R$^5$ wherein R$^5$ represents R, OR, SR, S-phenyl, S-phenyl-(R$^8$)m, SOR, SO$_2$R, CN, —O—COR, —NHCOR, —NRCOOR, —NRCONRR$^4$, —O—CONRR$^4$, —NRR$^4$, halo, or Y, wherein Y is a heterocycle selected from the group consisting of pyrimidinyl, pyridyl, imidazolyl, tetrazolyl, isothiazolyl and morpholinyl, and m is 1 to 4;

$R_2$ is independently —NHSO$_2$R$^6$; hydrogen; lower alkyl; —NHCOR$^6$; —NRR$^4$; —OR$^7$ wherein R$^7$ is H, R, lower alkenyl, lower alkynyl; —O—(CH$_2$)$_m$—O— when two adjacent R$^2$ are joined together to form a fused ring and where m represents 1, 2 or 3; halo; trihaloalkyl; —SO$_2$NRR$^4$; —SO$_2$NHY wherein Y is a heterocycle as defined; —SO$_2$NHX wherein X is —CONH$_2$, —CSNH$_2$ or —C(═NH)NH$_2$; —SO$_2$CF$_3$; —CN; —SO$_2$NR$^4$COR$^6$; or —COOR$^6$;

$R^3$ is independently hydrogen; hydroxy; lower alkyl; lower alkoxy; —OR$^7$; —O—(CH$_2$)$_m$—O— when two adjacent R$^3$ are joined together to form a fused ring and wherein m is 1, 2 or 3; halo; —O—CH$_2$-phenyl or phenyl substituted with R$^8$; —CH$_2$OR$^6$; —SR$^6$; —S—CH$_2$-phenyl or phenyl substituted with R$^8$; —CH$_2$—S—R$^6$; —SOR$^6$; —SO$_2$R$^6$; —OCOR$^6$; —NRR$^4$; —NH$_2$; —NR$^4$COOR$^6$; —NHCOR$^6$; or —OCOOR$^6$;

$R^6$ is selected from the group consisting of R, —$CF_3$, unsubstituted phenyl or phenyl substituted with $R^8$;

$R^8$ is independently hydrogen, lower alkyl, lower alkoxy, amino, lower alkylamino, lower di-alkyl amino, halo, cyano or halo substituted lower alkyl; and n is 1, 2 or 3; p is 1, 2 or 3.

12. The method of claim 11 wherein $R^1$ is —$(CH_2)_m R^5$.

13. The method of claim 12 wherein $R^5$ is Y.

14. The method of claim 13 wherein $R^5$ is a tetrazolyl substituted with $R^8$.

15. The method of claim 11 wherein $R^2$ is independently lower alkoxy, —$SO_2NRR^4$; —$SO_2NHX$ wherein X represents —$CONH_2$, —$CSNH_2$, or —$C(=NH)NH_2$; —$SO_2NHY$; —$SO_2CF_3$; —$SO_2NHCOR^6$; or —$OR^7$.

16. The method of claim 15 wherein $R^2$ is —$SO_2NRR^4$.

17. The method of claim 15 wherein $R^2$ is lower alkoxy.

18. The method of claim 11 wherein $R^3$ is independently hydrogen; lower alkyl; —$OR^7$; —O—$(CH_2)_m$—O— when two adjacent $R^3$ are joined together to form a fused ring and m is 1, 2 or 3; —$OCH_2$-phenyl or phenyl substituted with $R^8$; halogen; —$SR^6$; —$OCOR^6$; —$NHCOR^6$; or —$OCOOR^6$.

19. The method of claim 18 wherein $R^3$ is independently hydrogen; hydroxy; lower alkyl; lower alkoxy or halo especially —F.

20. The method of claim 19 wherein $R^3$ is independently hydrogen or —F.

21. A method for regulating apoptosis in human cells comprising exposing said cells to an effective amount of a compound of the formula:

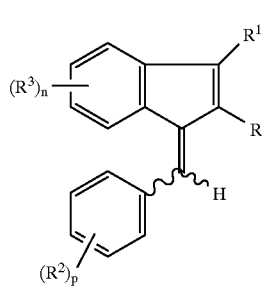

(I)

wherein

R is H, loweralkyl, trihaloalkyl or cycloalkyl;

$R^1$ is —$CHR^4COOR$ wherein $R^4$ is hydrogen, hydroxy, loweralkyl, amino, alkylamino or benzylamino; —CH=CHR; —$(CH_2)_m CONRR^4$; —CHOH—CHOH—R; —$(CH_2)_m R^5$ wherein $R^5$ represents R, OR, SR, S-phenyl, S-phenyl-$(R^8)m$, SOR, $SO_2R$, CN, —O—COR, —NHCOR, —NRCOOR, —$NRCONRR^4$, —O—$CONRR^4$, —$NRR^4$, halo, or Y, wherein Y is a heterocycle selected from the group consisting of pyrimidinyl, pyridyl, imidazolyl, tetrazolyl, isothiazolyl and morpholinyl, and m is 1 to 4;

$R_2$ is independently —$NHSO_2R^6$; hydrogen; lower alkyl; —$NHCOR^6$; —$NRR^4$; —$OR^7$ wherein $R^7$ is H, R, lower alkenyl, lower alkynyl; —O—$(CH_2)_m$—O— when two adjacent $R^2$ are joined together to form a fused ring and where m represents 1, 2 or 3; halo; trihaloalkyl; —$SO_2NRR^4$; —$SO_2NHY$ wherein Y is a heterocycle as defined; —$SO_2NHX$ wherein X is —$CONH_2$, —$CSNH_2$ or —$C(=NH)NH_2$; —$SO_2CF_3$; —CN; —$SO_2NR^4COR^6$; or —$COOR^6$;

$R^3$ is independently hydrogen; hydroxy; lower alkyl; lower alkoxy; —$OR^7$; —O—$(CH_2)_m$—O— when two adjacent $R^3$ are joined together to form a fused ring and wherein m is 1, 2 or 3; halo; —O—$CH_2$-phenyl or phenyl substituted with $R^8$; —$CH_2OR^6$; —$SR^6$; —S—$CH_2$-phenyl or phenyl substituted with $R^8$; —$CH_2$—S—$R^6$; —$SOR^6$; —$SO_2R^6$; —$OCOR^6$; —$NRR^4$; —$NH_2$; —$NR^4COOR^6$; —$NHCOR^6$; or —$OCOOR^6$;

$R^6$ is selected from the group consisting of R, —$CF_3$, unsubstituted phenyl or phenyl substituted with $R^8$;

$R^8$ is independently hydrogen, lower alkyl, lower alkoxy, amino, lower alkylamino, lower di-alkyl amino, halo, cyano or halo substituted lower alkyl; and n is 1, 2 or 3; p is 1, 2 or 3.

22. The method of claim 21 wherein $R^1$ is —$(CH_2)_m R^5$.

23. The method of claim 22 wherein $R^5$ is Y.

24. The method of claim 21 wherein $R^2$ is independently lower alkoxy, —$SO_2NRR^4$; —$SO_2NHX$ wherein X represents —$CONH_2$, —$CSNH_2$, or —$C(=NH)NH_2$; —$SO_2NHY$; —$SO_2CF_3$; —$SO_2NHCOR^6$; or —$OR^7$.

25. The method of claim 24 wherein $R^2$ is —$SO_2NRR^4$.

26. The method of claim 24 wherein $R^2$ is lower alkoxy.

27. The method of claim 21 wherein $R^3$ is independently hydrogen; lower alkyl; —$OR^7$; —O—$(CH_2)_m$—O— when two adjacent $R^3$ are joined together to form a fused ring and m is 1, 2 or 3; —$OCH_2$-phenyl or phenyl substituted with $R^8$; halogen; —$SR^6$; —$OCOR^6$; —$NHCOR^6$; or —$OCOOR^6$.

28. The method of claim 27 wherein $R^3$ is independently hydrogen; hydroxy; lower alkyl; lower alkoxy or halo especially —F.

29. The method of claim 28 wherein $R^3$ is independently hydrogen or —F.

* * * * *